US012385926B2

(12) United States Patent
Bermejo Martin et al.

(10) Patent No.: US 12,385,926 B2
(45) Date of Patent: Aug. 12, 2025

(54) MMP-8 AS A MARKER FOR IDENTIFYING INFECTIOUS DISEASE

(71) Applicants: B.R.A.H.M.S GmbH, Hennigsdorf (DE); Fundacion Instituto de Estudios de Ciencias de la Salud de Castilla y Leon, Soria (ES)

(72) Inventors: Jesus F. Bermejo Martin, Soria (ES); Eduardo Tamayo Gomez, Soria (ES); David Andaluz Ojeda, Soria (ES); Lydia Blanco Peris, Soria (ES); Alicia Ortega Andres, Soria (ES); Raquel Almansa Mora, Soria (ES)

(73) Assignees: B.R.A.H.M.S GmbH, Hennigsdorf (DE); Fundacion Instituto de Estudios de Ciencias de la Salud de Castilla y Leon, Soria (ES)

( * ) Notice: Subject to any disclaimer, the term of this patent is extended or adjusted under 35 U.S.C. 154(b) by 982 days.

(21) Appl. No.: 16/617,622

(22) PCT Filed: May 31, 2018

(86) PCT No.: PCT/EP2018/064363
§ 371 (c)(1),
(2) Date: Nov. 27, 2019

(87) PCT Pub. No.: WO2018/220129
PCT Pub. Date: Dec. 6, 2018

(65) Prior Publication Data
US 2020/0225248 A1     Jul. 16, 2020

(30) Foreign Application Priority Data
May 31, 2017  (EP) ..................... 17173724

(51) Int. Cl.
| | |
|---|---|
| C12Q 1/6883 | (2018.01) |
| A61K 31/43 | (2006.01) |
| A61K 31/431 | (2006.01) |
| A61K 31/7048 | (2006.01) |
| A61K 35/00 | (2006.01) |
| A61K 36/00 | (2006.01) |
| G01N 33/68 | (2006.01) |
| C07G 11/00 | (2006.01) |

(52) U.S. Cl.
CPC ....... *G01N 33/6893* (2013.01); *C12Q 1/6883* (2013.01); *G01N 2333/988* (2013.01); *G01N 2800/102* (2013.01); *G01N 2800/26* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | |
|---|---|---|
| 2004/0029176 A1 | 2/2004 | Yoon |
| 2010/0292131 A1 | 11/2010 | Kas et al. |
| 2014/0377777 A1 | 12/2014 | Anderberg et al. |

FOREIGN PATENT DOCUMENTS

| | | |
|---|---|---|
| WO | 02/42770 A1 | 5/2002 |
| WO | 2009/062948 A1 | 5/2009 |
| WO | 2013/086359 A1 | 6/2013 |

OTHER PUBLICATIONS

Mokline, A., et al. Ann. Burns Fire Disaster;XXXVIII(2):116-120 (Year: 2015).*
Pramod, J. and Singh, A. Am. J. Med.;121(6):e11 (Year: 2008).*
Moore, L.J., et al. Trauma;70(3):672-680 (Year: 2011).*
Sheikh, Z (WebMD, 2024, 4 pages) (Year: 2024).*
NIH (2024, one page) (Year: 2024).*
Thrailkill et al (Clin. Chem. Lab. Med., 2005 43: 1392-1399) (Year: 2005).*
D.M. Maslove et al., "Gene Expression Profiling in Sepsis: Timing, Tissue, and Translational Considerations", Trends in Molecular Medicine, vol. 20, No. 4 (Apr. 2014).
A. Lauhio et al., "Serum MMP-8, -9 and TIMP-1 in Sepsis: High Serum Levels of MMP-8 and TIMP-1 are Associated with Fatal Outcome in a Multicentre, Prospective Cohort Study. Hypothetical Impact of Tetracyclines", Pharmacological Research, vol. 64 (2011) pp. 590-594.

(Continued)

*Primary Examiner* — Misook Yu
*Assistant Examiner* — Marianne DiBrino
(74) *Attorney, Agent, or Firm* — Ryan Pool

(57) ABSTRACT

The invention relates to a method for the diagnosis, prognosis, risk assessment, risk stratification, monitoring, therapy guidance and/or therapy control of an infectious disease in a subject, wherein said method comprises providing a sample of said subject; determining a level of matrix metalloprotease-8 (MMP-8) or fragment(s) thereof in a sample of said subject, wherein said level of MMP-8 or fragment(s) thereof distinguishes between the presence and absence of an infectious disease in a patient with symptoms of a systemic inflammatory condition. In a preferred embodiment the invention relates to the determination of procalcitonin (PCT) and MMP-8 and their combined use to distinguish between the presence and absence of infectious disease in patients with symptoms of systemic inflammatory condition. The invention also relates to a computer-implemented method and a kit for conducting the method of the invention.

12 Claims, 4 Drawing Sheets

(56) References Cited

OTHER PUBLICATIONS

Figure 1:
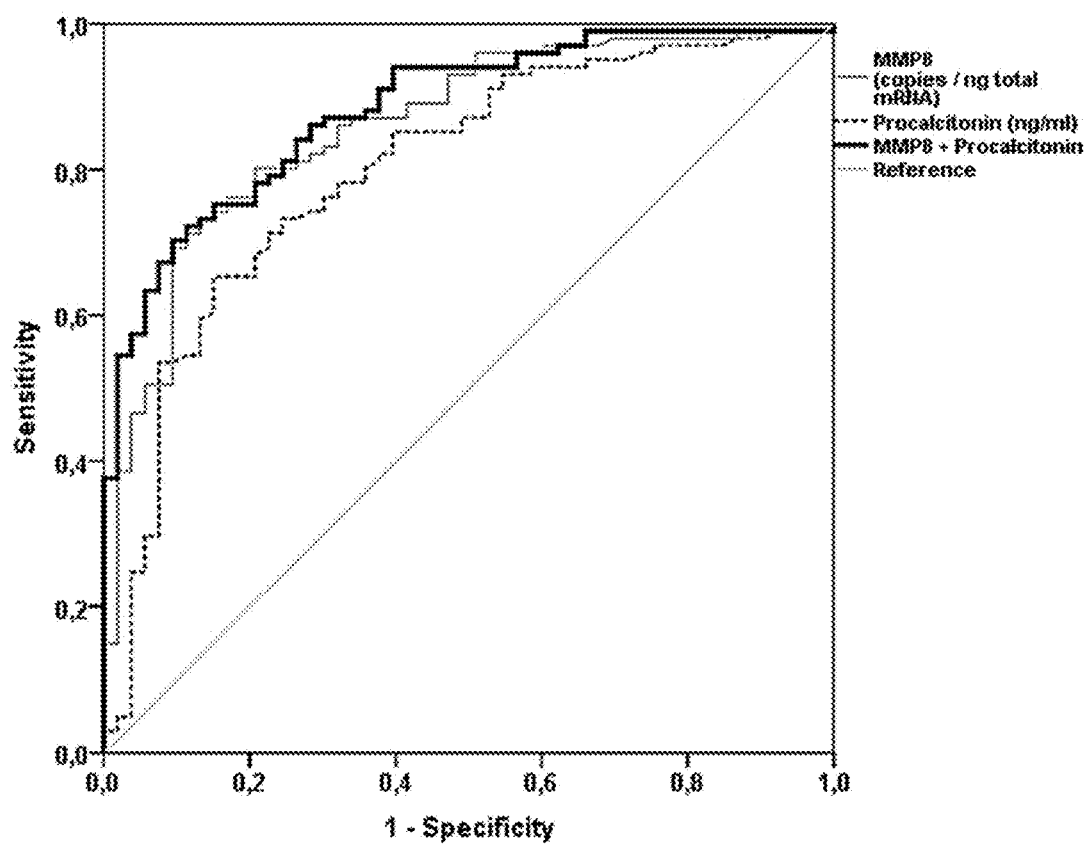
Figure 1:
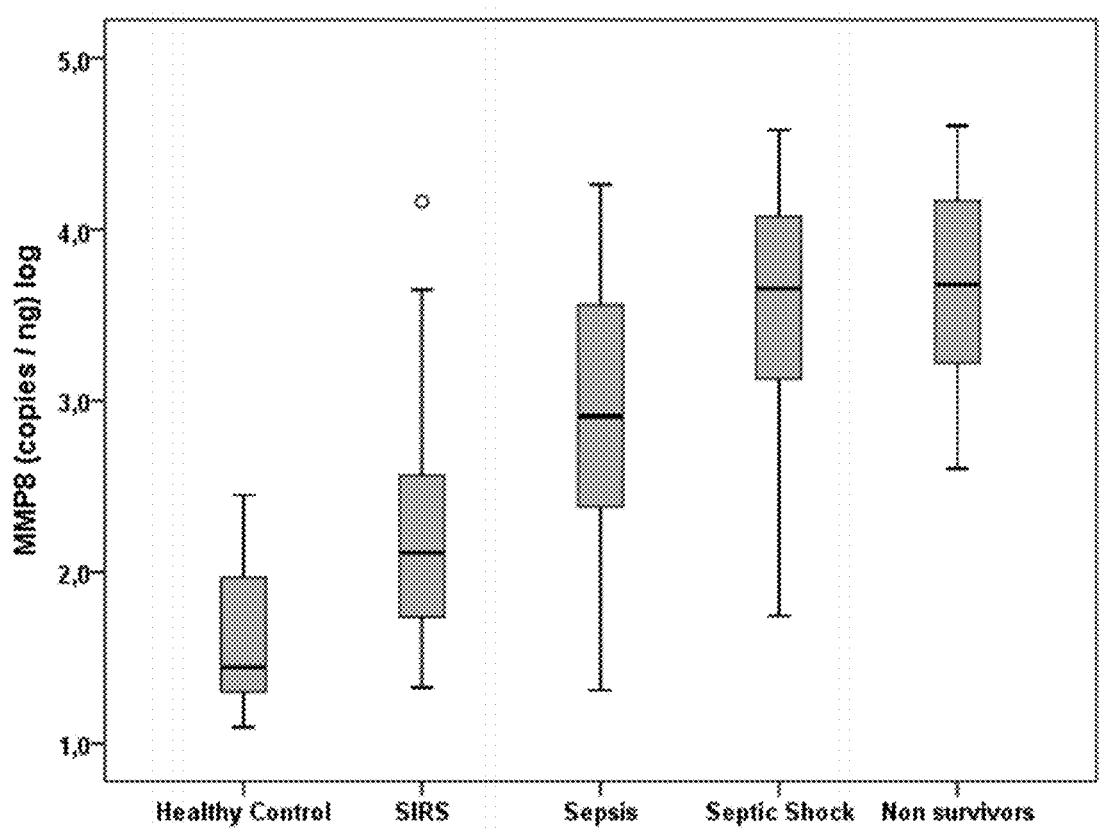

V. Castro-Leyva et al., "Preserved Ex Vivo Inflammatory Status in Decidual Cells from Women with Preterm Labor and Subclinical Intrauterine Infection", PLOS One, vol. 7, No. 8 (Aug. 2012) pp. e43605.

H.R. Wong, "Clinical Review: Sepsis and Septic Shock—The Potential of Gene Arrays", Critical Care, vol. 16 (2012) pp. 204-211.

* cited by examiner

A

B

C

| SIRS vs Sepsis | AUROC | p |
|---|---|---|
| MMP-8 | 0,860 | <0,001 |
| PCT | 0,801 | <0,001 |
| MMP-8+PCT | 0,885 | <0,001 |

MMP-8 AS A MARKER FOR IDENTIFYING INFECTIOUS DISEASE

The invention relates to a method for the diagnosis, prognosis, risk assessment, risk stratification, monitoring, therapy guidance and/or therapy control of an infectious disease in a subject, wherein said method comprises providing a sample of said subject; determining a level of matrix metalloprotease-8 (MMP-8) or fragment(s) thereof in a sample of said subject, wherein said level of MMP-8 or fragment(s) thereof distinguishes between the presence and absence of an infectious disease in a patient with symptoms of a systemic inflammatory condition. In a preferred embodiment the invention relates to the determination of procalcitonin (PCT) and MMP-8 and their combined use to distinguish between the presence and absence of infectious disease in patients with symptoms of systemic inflammatory condition. The invention also relates to a computer-implemented method and a kit for conducting the method of the invention.

BACKGROUND OF THE INVENTION

A dysregulated host response to an infection can lead to various clinical manifestations, including potentially organ dysfunction and/or shock. One particular category of misregulated immune response to an infection relates to sepsis or septic shock. Septic disorders affect millions of people worldwide. The number of incidents continues to increase and therefore the need to improve the prevention, diagnosis and management of sepsis or severe infections is significant.

Sepsis has a time-critical clinical course whereby an early diagnosis of the disease is essential to initiate the required therapy and clinical management of sepsis. Every additional hour it takes to administer antibiotics and perform other key steps in sepsis treatment increases the odds of death by 4 percent (Seymour et al, N Engl J Med. 2017 May 21). Sepsis can develop quickly, leading to organ damage or multi-organ damage or shock. As such, early determination of an infection and initiation of appropriate treatment is crucial.

Sepsis can begin with vague symptoms, including shivering, a fever or feeling very cold; clammy or sweaty skin; confusion or disorientation; a rapid heartbeat or pulse; confusion or disorientation; shortness of breath; or simply extreme pain or discomfort. During the onset of sepsis, a complex inflammatory response occurs in the initial phase. The pro-inflammatory response is characterized by an interaction of different mediators such as growth factors, cytokines and chemokines and different cell types such as neutrophils, macrophages or different tissue cells. Therefore, biomarkers can be used to improve diagnosis and to support patient management (Rhodes et al., Crit Car Med, 2017 Vol. 45 (3) 486-552).

Despite having long been recognized as a dangerous disease, approximately 60,000 cases lead to death per year in Germany alone. After heart attack, sepsis represents the third most common cause of death and the seventh most common diagnosis of a life-endangering disease. In 2011, 87,000 patients were diagnosed with sepsis, 69,000 with a severe sepsis and 19,000 with septic shock. In approximately 70% of the cases a nosocomial infection was identified as the cause. 10.5% of patients with a sepsis and 42.8% of patients with a severe sepsis ultimately died of the disease.

Sepsis can be divided into sepsis, severe sepsis or septic shock. The basis for the different diagnoses is provided by the American College of Chest Physicians (ACCP) in the Society of Critical Care Medicine (SCCM). According to traditional diagnostic criteria, sepsis is diagnosed when an infection is present and at least two criteria of a systemic inflammatory response syndrome (SIRS) are present. SIRS symptoms relate to fever over 38° C. or below 36° C., increased heart rate above 90 beats per minute, Tachypnea with a respiratory rate of >than 20/min or $PaCO_2$<32 mmHg (4.3 kPa), hyperventilation, a leucocytosis ($\geq$than 12.000/$mm^3$) or a leucopenia ($\leq$4.000/$mm^3$). When in addition to these criteria additional organ dysfunction such as an acute thrombocytopenia or arterial hypoxia or renal dysfunction are identified, for example by determining the Quick Sequential Organ Failure Assessment (qSOFA) or other parameter with the potential for clinical evaluation of organ status, then an infection with organ dysfunction or a severe sepsis can be diagnosed. The most serious form of the disease is considered as septic shock, which is defined by a 40-60% rate of death and is characterized by a severe breakdown in circulation.

Recently, new guidelines for diagnosing/defining sepsis have been issued (refer to Singer et al., JAMA. 2016; 315 (8): 801-810), according to which the emphasis on SIRS criteria is reduced and the diagnosis is more closely based on Sequential Organ Failure Assessment (such as SOFA or qSOFA (3 criteria instead of 6 (SOFA)). Although such definitions may provide a more accurate representation of sepsis with respect to predictions of mortality, they are of little practical diagnostic help, as the generation of SOFA scores is more complicated and time consuming, in some cases requiring molecular and/or behavioural assessment of respiration, coagulation, liver function, cardiovascular system, central nervous system and renal performance (Slesinger and Dubensky, "Sepsis-3, a New Definition. Solutions or New Problems?", in a newsletter of the American College of Emergency Physicians).

For example, qSOFA was derived to be a predictor of mortality and not a diagnostic or immediate prognostic screening tool. Considering early recognition and treatment are crucial to improved survival in sepsis, qSOFA appears problematic in the ED or ICU settings, as it can lead to delayed diagnosis and initiation of treatment.

One clinically crucial aspect is to differentiate patients with symptoms of a systemic inflammatory condition, such as systemic inflammatory response syndrome (SIRS), versus patients with infections or sepsis. As described above, the symptoms of infectious disease and sepsis are essentially very similar to those of systemic inflammatory conditions, such as SIRS without infection, thereby presenting difficulties to medical practitioners. This represents a significant problem for medical practitioners in particular in emergency or intensive care settings, in electing appropriate treatments and/or management of patients with symptoms of systemic inflammatory conditions. The identification of an infection in patients with SIRS symptoms in a fast and reliable manner is crucial in providing the appropriate medical care.

In the prior art, WO 2009/062948 discloses a method for predicting or diagnosing sepsis comprising analysis of pro-hepcidin using a reference level from a patient having SIRS. WO 2009/062948 also discloses using procalcitonin (PCT) as an additional marker in the context of the disclosed method. In contrast to the method described in WO 2009/062948, the method of the present invention is based on the surprising finding that MMP-8 can be used to identify patients suffering from an infectious disease from a pool of patients displaying symptoms of a systemic inflammatory condition, as disclosed herein. There is no hint in the art that MMP-8 could be useful in the context of such a method.

MMP-8 has been described as being associated with infectious diseases and inflammation. MMP-8 has been identified as being upregulated in sepsis and correlating with disease severity (Maslove et al., Trends in Molecular Medicine, 20:4, Apr. 1, 2014). High serum levels of MMP-8 have been reported to be associated with fatal outcome in patients with sepsis (Lauhio et al., Pharmacological Research, 64:6, Jun. 1, 2011). A further study compared the inflammatory response in women with preterm labour and identified a significant increase of MMP-8 and MMP-9 in the supernatants of decidual cells isolated from women with subclinical intrauterine infection (Castro-Leyva et al., PLOS One, 7:8, Aug. 22, 2012). Also, it has been described that MMP-8 is highly expressed in patients with septic shock and that inhibition of MMP-8 activity confers a survival advantage in models of sepsis (Wong et al., Critical Care, 16, Jan. 1, 2012). However, the possibility of using MMP-8 for differentiating between an infection and a non-infectious inflammation has neither been described nor suggested in the art.

Kits and reagents for determining MMP-8 in a sample have been described in the art (WO 2013/086359 A1; WO 2002/42770). However, such kits do not comprise reference data corresponding to MMP-8 levels in patients with a systemic inflammatory condition without an infection, which are required for using such a kit in the context of the method of the present invention.

A need therefore exists in the field of infectious diseases and inflammation for additional means for identifying infectious disease and differentiation between patients presenting symptoms of systemic inflammatory condition either with or without infectious disease.

SUMMARY OF THE INVENTION

In light of the difficulties in the prior art, the technical problem underlying the invention is the provision of means for differentiating between the presence and absence of an infectious disease in patients with symptoms of a systemic inflammatory condition.

The present invention therefore seeks to provide a method, kit and further means for diagnosis, prognosis, risk assessment, risk stratification, monitoring, therapy guidance and/or therapy control of infectious disease, and differentiation from patients with symptoms of systemic inflammatory condition but without an infectious disease, on the basis of matrixmetalloproteinase-8 (MMP-8) levels determined in a sample from a patient. One object of the invention is therefore the use of a biomarker or combination of biomarkers to distinguish patients with an infection or sepsis patients from SIRS patients and to indicate the disease severity.

The solution to the technical problem of the invention is provided in the independent claims. Preferred embodiments of the invention are provided in the dependent claims.

The invention therefore relates to a method for the diagnosis, prognosis, risk assessment, risk stratification, monitoring, therapy guidance and/or therapy control of an infectious disease in a subject, wherein said method comprises:
Providing a sample of said subject;
determining a level of matrix metalloprotease-8 (MMP-8) or fragment(s) thereof in a sample of said subject,
wherein said level of MMP-8 or fragment(s) thereof distinguishes (differentiates) between the presence and absence of an infectious disease in a patient with symptoms of a systemic inflammatory condition.

It was entirely surprising that MMP-8 is not only suitable for the identification of an infectious disease in a patient, but also that it may be employed to distinguish (differentiate) between the presence and absence of an infectious disease in a patient with symptoms of a systemic inflammatory condition. The present invention is therefore preferably related to a differential diagnosis, enabling medical practitioners to determine whether or not an infectious disease is evident in a patient with symptoms of systematic inflammation. Subsequently, the method of the invention enables a fast, and more tailored medical treatment upon identifying whether or not an infectious disease is present. For example, the method of the invention leads to the avoidance of unnecessary antibiotic or other anti-infectious treatment upon observing symptoms of a systematic inflammation.

The present invention is based on the completely unexpected observation that levels of MMP-8 can be used to identify patients suffering from an infectious disease from among a potentially larger unrefined group of patients displaying symptoms of a systemic inflammatory condition. Although the possibility of differentiating these respective patient populations has been suggested for other markers, there is no indication that MMP-8 could be used in the context of such a method. It is evident to a skilled person that properties of a certain biomarker and observed associations or correlations cannot be transferred or extrapolated to other, unrelated biomarkers. Accordingly, the fact that MMP-8 levels are useful for differentiating patients suffering from an infectious disease and displaying symptoms of a systemic inflammatory condition from patients displaying symptoms of a systemic inflammatory condition and not suffering from an infectious disease is surprising and unexpected, even if the use other biomarkers for this purpose may have been described.

In a preferred embodiment of the invention the method as described herein additionally comprises determining a level of procalcitonin (PCT) or fragment(s) thereof in a sample of the subject, wherein said level of procalcitonin or fragment(s) thereof and the level of MMP-8 or fragment(s) thereof differentiate between the presence and absence of an infectious disease in a patient with symptoms of a systemic inflammatory condition. The invention is therefore also based on the unexpected finding that MMP-8 levels in combination with PCT levels, compared to MMP-8 levels or PCT levels alone, enable a more reliable diagnosis of an infection in patients with a systemic inflammatory condition.

As demonstrated in the examples below, the combined use of procalcitonin as a biomarker for sepsis or an infectious disease together with MMP-8 provides even more certainty in the differentiation between the presence and absence of an infectious disease in a patient with symptoms of a systemic inflammatory condition. MMP-8 and PCT may therefore be observed to represent synergistic biomarkers, which unexpectedly enable higher statistical certainty. This represents a surprising finding, as biomarkers for sepsis are typically not synergistic or complementary, but represent mere alternative diagnostic markers.

The combined employment of PCT in combination with MMP-8 may be realised either in a single multiplex assay, or in two separate assays conducted on a sample form the patient. The sample may relate to the same sample, or to different samples. The assay employed for the detection and determination of PCT and MMP-8 may also be the same or different, for example an immunoassay may be employed for the determination of one of the above markers, and an assay based on the determination of a corresponding nucleic acid may be used for the determination of the other marker. More detailed descriptions of suitable protein and nucleic acid assays are provided below. Combined use may encompass parallel, simultaneous or subsequent analysis of the two (or more) markers. The values obtained for both markers may in any way appropriate be analysed and their diagnostic value combined in any appropriate manner.

In one embodiment of the method described herein the determined level of MMP-8 or fragment(s) thereof is indicative of the presence of an infectious disease in a patient with symptoms of a systemic inflammatory condition, when said determined level(s) is above a reference level (such as a threshold or cut-off value and/or a population average) corresponding to MMP-8 in patients with a systemic inflammatory condition without an infection.

In one embodiment of the method described herein the determined levels of MMP-8 or fragment(s) thereof in combination with the determined levels of PCT or fragment(s) thereof are indicative of the presence of an infectious disease in a patient with symptoms of a systemic inflammatory condition, when one or more of said determined level(s) are above a reference level (threshold or cut-off value and/or a population average) corresponding to MMP-8, and to PCT respectively, in patients with a systemic inflammatory condition without an infection.

In such embodiments the reference level corresponds to a biomarker value/level in patients with a systemic inflammatory condition without an infection. As such, the employment of a reference level for such patients differentiates the present invention in a surprising and beneficial manner from the prior art. The invention is therefore based on the unexpected finding that MMP-8 levels in patients with a systemic inflammatory condition but with an infection are typically higher compared to MMP-8 levels in patients with similar symptoms but without an infection. Additionally, the converse of this scenario is analogously applicable, namely MMP-8 levels in patients with a systemic inflammatory condition but without an infection are typically reduced compared to MMP-8 levels in patients with similar symptoms but with an infection.

In one embodiment of the method described herein the determined level of MMP-8 or fragment(s) thereof is indicative of the absence of an infectious disease in a patient with symptoms of a systemic inflammatory condition, when said determined level(s) is below a reference level (threshold or cut-off value and/or a population average) corresponding to MMP-8 in patients with a systemic inflammatory condition with an infection.

In one embodiment the invention is characterised in that the applicable reference level is not related to MMP-8 levels in healthy control patients. Patients with symptoms of a systemic inflammatory condition will inherently show elevated MMP-8 levels above those of healthy patients. The prior art teaches that MMP-8 is present in greater amounts in serum samples when assessed via ELISA from septic patients compared to healthy controls (Anneli Lauhio et al., Pharmacological Research 64, 2011; 590-594). For example, the median serum MMP-8 (ng/ml) levels for severe sepsis or septic shock patients (n=248) were significantly higher than those of healthy controls (n=10) [71.70 (0-1651) vs. 2.320 (0-16.33) p<0.0001]. Mean (±SEM) serum MMP-8 (ng/ml) levels for severe sepsis or septic shock patients, who did not survive (n=33), were also significantly higher when compared to serum MMP-8 levels of those who survived (n=215) (242.6±41.5 vs. 134.6±13.9, p=0.0062).

However, the surprising finding of the invention is the differentiation in MMP-8 levels between patients with or without infection, when patients show symptoms of a systematic inflammatory condition. In a preferred embodiment the reference level of MMP-8 corresponds to those levels determined in patients with symptoms of a systemic inflammatory condition but without an infection, namely SIRS patients without an infection. Determination of MMP-8 levels above such a reference indicates the presence of an infection or sepsis and the absence of an infection-free SIRS.

The reference level corresponding to MMP-8 in patients with a systemic inflammatory condition without an infection may vary depending on the particular diagnostic assay employed. A skilled person is capable of determining such a reference level for any given analytical/diagnostic approach. For example, reference levels will depend on the sensitivity and accuracy of the analytical technique employed, and will depend on the type of method used, for example differences will obviously arise between determining for example mRNA encoding MMP-8 in a sample compared to determination of protein levels.

In one embodiment the reference level may be a cut-off level or a mean fold change (fold change), wherein when MMP-8 levels above the cut-off level or a particular fold change are determined, the assay indicates the presence of an infection. A range of potential cut-off or fold change values appears suitable in light of variation in patient levels and analytic techniques.

In one embodiment of the invention, the cut-off level for MMP-8 may be a value in the range of 0.001 to 500 ng/ml, or 0.01 to 500 ng/ml, in a serum or plasma sample, when using for example a Luminex MAGPIX Assay, preferably from E-Bioscience, or an ELISA assay for determining MMP-8 levels, preferably in a blood sample or sample derived from blood, such as those described herein. In a preferred embodiment the cut-off level of MMP-8 may be in the range of 0.005 to 400, 0.01 to 300, 0.032 to 350, 0.05 to 300, 0.05 to 200, 0.1 to 100, 0.1 to 50, 0.1 to 20, or 0.2 to 2 ng/ml, or preferably 0.032 to 0.3 ng/ml. Any value within these ranges may be considered as an appropriate cut-off value. For example, 0.005, 0.01, 0.03, 0.04, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 6, 7, 8, 9, 10, 15, 20, 25, 30, 35, 40, 45, 50, 55, 60, 65, 70, 75, 80, 85, 90, 95, 100, 120, 140, 160, 180, 200, 250, 300, 350, 400, 450, or 500 ng/mL may be employed.

Such a cut-off value is one non-limiting embodiment of the MMP-8 reference level corresponding to MMP-8 levels in patients with symptoms of a systematic inflammatory condition without an infection.

Alternatively, in some embodiments, cut-off levels may be employed as follows:

In preferred embodiments, the cut-off levels are those disclosed in Table 2. These values are relevant preferably for determination of MMP-8 levels using an ELISA assay, but may also apply for other detection means.

For example, an optimal combination of sensitivity and specificity is represented by the highest youden index. As can be determined from Table 2, to rule out sepsis a sensitivity of 100% (cutoff 3.28 ng/ml) is preferred, to rule-in sepsis a specificity of 100% (cutoff 43.68 ng/ml) is preferred.

In preferred embodiments, preferably using an ELISA detection system, a cut-off value for ruling out infections (e.g. sepsis) in patients with symptoms of systemic inflammation may therefore be any value of MMP8 of or below 10 ng/ml, preferably below 9, 8, 7, 6, 5 or 4 ng/ml, or more preferably of or below 3.28 ng/ml. For example, a patient with an MMP8 level below the indicated threshold indicates the absence of an infection (e.g. sepsis) in a patient with symptoms of systemic inflammation.

In preferred embodiments, preferably using an ELISA detection system, a cut-off value for ruling in infections (e.g. sepsis) in patients with symptoms of systemic inflammation may therefore be any value of MMP8 of or above 10 ng/ml, preferably above 12, 14, 16, 18, 20, 24, 28, 32, 36 or 40 ng/mL, or more preferably of or above 43.68 ng/ml. For example, a patient with an MMP8 level above the indicated threshold (cut-off) indicates the presence of an infection (e.g. sepsis) in a patient with symptoms of systemic inflammation.

In preferred embodiments, preferably using an ELISA detection system, a cut-off value for determining the presence of an infection (e.g. sepsis) in patients with symptoms of systemic inflammation may therefore be any value of MMP8 in the range of 10-500 ng/ml, 10-60 ng/mL, or 20-50 ng/ml, preferably 12-46, 14-42, 16-38, 18-34, 20-30 or 22-26 ng/ml, or more preferably between 23 and 25 ng/ml. For example, a patient with an MMP8 level above an indicated threshold (cut-off) in the provided range indicates the presence of an infection (e.g. sepsis) in a patient with symptoms of systemic inflammation.

In some embodiments, corresponding values from Table 6 for the ELISA measurements may also be derived. In some embodiments, preferably using an ELISA detection system, a cut-off value for determining the presence of an infection (e.g. sepsis) in patients with symptoms of systemic inflammation may therefore be any value of MMP8 in the range of 15-500 ng/ml, 15-100 ng/mL, or 15-75 ng/ml, preferably 15-75, or 25-75 ng/ml, or more preferably between 30 and 70 ng/mL. For example, a patient with an MMP8 level above an indicated threshold (cut-off) in the provided range indicates the presence of an infection (e.g. sepsis) in a patient with symptoms of systemic inflammation.

Alternatively, in some embodiments, cut-off levels may be employed as follows:

In preferred embodiments, the cut-off levels are those disclosed in Table 6. These values are relevant preferably for determination of MMP-8 levels using a Luminex MAGPIX E-Bioscience Assay, but may also apply for other detection means.

For example, an optimal combination of sensitivity and specificity is represented by the highest youden index. As can be determined from Table 6, to rule out sepsis a sensitivity of 100% or value close thereto (cutoff 32.98 pg/mL) is preferred, to rule-in sepsis a specificity of 100% or value close thereto (cutoff 211.60 pg/mL) is preferred.

In preferred embodiments, preferably using a Luminex MAGPIX E-Bioscience Assay, a cut-off value for ruling out infections (e.g. sepsis) in patients with symptoms of systemic inflammation may therefore be any value of MMP8 of or below 70 pg/mL, preferably below 60, 50 or 40 pg/mL. For example, a patient with an MMP8 level below the indicated threshold indicates the absence of an infection (e.g. sepsis) in a patient with symptoms of systemic inflammation.

In preferred embodiments, preferably using a Luminex MAGPIX E-Bioscience Assay, a cut-off value for ruling in infections (e.g. sepsis) in patients with symptoms of systemic inflammation may therefore be any value of MMP8 of or above 100 pg/mL, preferably above 125, 150, 175, or 200 pg/mL. For example, a patient with an MMP8 level above the indicated threshold (cut-off) indicates the presence of an infection (e.g. sepsis) in a patient with symptoms of systemic inflammation.

In preferred embodiments, preferably using a Luminex MAGPIX E-Bioscience Assay, a cut-off value for determining the presence of an infection (e.g. sepsis) in patients with symptoms of systemic inflammation may therefore be any value of MMP8 in the range of 100-300 pg/mL, or 150-250 pg/mL. For example, a patient with an MMP8 level above an indicated threshold (cut-off) in the provided range indicates the presence of an infection (e.g. sepsis) in a patient with symptoms of systemic inflammation.

With respect to a mean fold change, the mean fold change value may be applied analogously to a cutoff value. Fold change (used interchangeably with mean fold change) is a measure describing how much a quantity changes going from an initial to a final value. In other words, if a certain fold change in the amount of MMP-8 is detected over a reference level, this fold change value may be indicative of the presence of infectious disease. Fold changes can be calculated between two populations groups, and therefore be employed analogously to cut-offs.

In one embodiment of the invention, the fold change of MMP-8 may be a value in the range of a 0.2 to 100-fold increase in MMP-8 levels over a reference value for patients with symptoms of systemic inflammation without an infection. In a preferred embodiment the fold change of MMP-8 may be in the range of a 0.2 to 100 fold change, a 1 to 100 fold change, a 1.5 to 100 fold change, a 1.5 to 80 fold change, a 2 to 50 fold change, a 2 to 10 fold change, or a 3 to 5 fold change (increase). Any value within these ranges may be considered as an appropriate fold change value. For example, a fold change of 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.2, 4.4, 4.6, 4.8, 5, 5.2, 5.4, 5.6, 5.8, 6, 6.5, 7, 8, 9, 10, 20, 30, 40, 50, 60, 70, 80, 90, 100 may be employed.

Preferably, to distinguish between non-infected dyspnea vs. sepsis, a 2 to 5-fold change (increase), preferably a 2.75-4.27-fold change (increase), in MMP-8 levels is evident in sepsis; for the differentiation between non-infected dyspnea vs. severe sepsis or sepsis with organ dysfunction a 4 to 6-fold change (increase), preferably a 4.48 to 5.77-fold change (increase), is evident.

In preferred embodiments, the fold changes values, which may be used as cut-off levels, are those disclosed in Tables 1 and 5.

In preferred embodiments, a fold-change value (also to be used potentially as a cut-off value) for determining the presence of an infection (e.g. sepsis) in patients with symptoms of systemic inflammation may therefore be a 2- to 8-fold increase, preferably a 2.5- to 6-fold increase in MMP8 levels, compared to control values. For example, a patient with a 2- to 8-fold increase in MMP8 levels over MMP8 levels from a SIRS, dyspnea or other control subject with symptoms of systemic inflammation, indicates the presence of an infection (e.g. sepsis). These values may apply to either Luminex or ELISA methods (preferably from blood or blood-derived samples) and employ for example comparisons preferably between sepsis, or severe sepsis, compared to dyspnea. These changes relate to fold changes with 95% confidence interval (95% CI).

In preferred embodiments, PCT shows fold changes of 2- to 5-fold increases in PCT in sepsis patients over dyspnea reference values. In preferred embodiments, PCT shows fold changes of 5- to 25-fold, preferably 10- to 20-fold increases in PCT in severe sepsis patients over dyspnea reference values.

It was entirely surprising that a level of MMP8 could be correlated with the likelihood of the presence or absence of an infection (e.g. sepsis) in a patient with symptoms of systemic inflammation. Some fluctuation in the particular cut-off or fold change values as mentioned herein is contemplated, as the values may depend on multiple parameters such as the time point of sample isolation, the complicating diagnosis of one or more SIRS symptoms, in addition to the method used for determining the level of proADM or fragments thereof in said sample.

The cut-off and fold change values disclosed herein refer preferably to measurements of the protein level of MMP8 and/or PCT in a blood sample, preferably a whole blood sample or plasma or serum sample obtained from a patient, by means of ELISA or Luminex MAGPIX E-Bioscience Assay. Accordingly, the values disclosed herein may vary to some extent depending on the detection/measurement method employed, and the specific values disclosed herein are intended to also read on the corresponding values determined by other methods.

In embodiments of the invention, deviations from these possible cut-off or fold-change values are also claimed, such as deviations of +30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1%. These deviations apply to any one or more of the particular values indicated above.

The lower limit of detection of the Luminex MAGPIX E-Bioscience Assay is approximately 32 pg/mL, such that the cut-off or detectable levels for the fold change is clearly within the detectable range. Alternative assays for determining MMP-8 levels are also intended, as described in more detail below.

Cut-off values and other reference levels of MMP-8 in patients with symptoms of a systematic inflammatory condition without an infection may be determined by previously described methods. For example, methods are known to a skilled person for using the Coefficient of variation in assessing variability of quantitative assays in order to establish reference values and/or cut-offs (George F. Reed et al., Clin Diagn Lab Immunol. 2002; 9 (6): 1235-1239).

Additionally, functional assay sensitivity can be determined in order to indicate statistically significant values for use as reference levels or cut-offs according to established techniques. Laboratories are capable of independently establishing an assay's functional sensitivity by a clinically relevant protocol. "Functional sensitivity" can be considered as the concentration that results in a coefficient of variation (CV) of 20% (or some other predetermined % CV), and is thus a measure of an assay's precision at low analyte levels. The CV is therefore a standardization of the standard deviation (SD) that allows comparison of variability estimates regardless of the magnitude of analyte concentration, at least throughout most of the working range of the assay.

Furthermore, methods based on ROC analysis can be used to determine statistically significant differences between two clinical patient groups. Receiver Operating Characteristic (ROC) curves measure the sorting efficiency of the model's fitted probabilities to sort the response levels. ROC curves can also aid in setting criterion points in diagnostic tests. The higher the curve from the diagonal, the better the fit. If the logistic fit has more than two response levels, it produces a generalized ROC curve. In such a plot, there is a curve for each response level, which is the ROC curve of that level versus all other levels. Software capable of enabling this kind of analysis in order to establish suitable reference levels and cut-offs is available, for example JMP 12, JMP 13, Statistical Discovery, from SAS.

Cut off values may similarly be determined for PCT. Literature is available to a skilled person for determining an appropriate cut-off, for example Philipp Schuetz et al. (BMC Medicine. 2011; 9:107) describe that at a cut-off of 0.1 ng/mL, PCT had a very high sensitivity to exclude infection. Terence Chan et al. (Expert Rev. Mol. Diagn. 2011; 11 (5), 487.496) described that indicators such as the positive and negative likelihood ratios, which are calculated based on sensitivity and specificity, are also useful for assessing the strength of a diagnostic test. Values are commonly graphed for multiple cut-off values (CVs) as a receiver operating characteristic curve. The area under the curve value is used to determine the best diagnostically relevant CV. This literature describes the variation of CVs (cut-off values, that is dependent on the assay and study design), and suitable methods for determining cut-off values.

Population averages in MMP-8 levels may also be used as reference values, for example mean MMP-8 population values, whereby a control population of SIRS patients, or other group showing systemic inflammation without an infection, is used as a control, wherein the control group preferably comprises more than 10, 20, 30, 40, 50 or more subjects.

In one embodiment of the invention, the cut-off level for PCT may be a value in the range of 0.01 to 100.00 ng/ml in a serum sample, when using for example a Luminex MAGPIX E-Bioscience Assay or the BRAHM PCT-Kryptor Assay. In a preferred embodiment the cut-off level of PCT may be in the range of 0.01 to 100, 0.05 to 50, 0.1 to 20, or 0.1 to 2 ng/ml, and most preferably >0.05 to 0.5 ng/ml. Any value within these ranges may be considered as an appropriate cut-off value. For example, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 6, 7, 8, 9, 10, 15, 20, 25, 30, 35, 40, 45, 50, 55, 60, 65, 70, 75, 80, 85, 90, 95 or 100 ng/ml may be employed. In some embodiments, PCT levels for healthy subjects are approximately 0.05 ng/ml.

The preferred range for PCT cutoff levels for local (non-systematic) infectious disease lies in the range of 0.05 to 0.5 ng/ml. Values of greater than or equal to 0.05 ng/ml are indicative of an infection, whereas levels of greater than or equal to 0.5 ng/mL typically indicate a sepsis.

With respect to a mean fold change, the mean fold change value may be applied analogously to a cutoff value. In other words, if a certain fold change in the amount of PCT is detected over a reference level, this fold change value may be indicative of the presence of infectious disease.

In one embodiment of the invention, the fold change of PCT may be a value in the range of a 0.2 to 100-fold increase in PCT levels over a reference value for patients with symptoms of systemic inflammation without an infection. In a preferred embodiment the fold change of PCT may be in the range of a 0.2 to 100 fold change, a 1 to 100 fold change, a 1.5 to 100 fold change, a 2 to 100 fold change, a 2 to 80 fold change, a 2 to 60 fold change, or a 3 to 50 fold change (increase). Any value within these ranges may be considered as an appropriate fold change value. For example, a fold change of 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.2, 4.4, 4.6, 4.8, 5, 5.2, 5.4, 5.5, 5.6, 5.8, 6, 6.5, 7, 8, 9, 10, 11, 12, 16, 17, 18, 20, 30, 40, 50, 53, 60, 70, 80, 90, 100 may be employed.

Preferably, to distinguish between non-infected SIRS vs. sepsis, a 4 to 60-fold increase, preferably a 15.5-fold change, or a fold change in the range of a 4.8 to 49.5-fold change (increase), in PCT levels are evident in sepsis patients; for the differentiation between non-infected SIRS vs. sepsis.

Preferably, to distinguish between non-infected dyspnea vs. sepsis, a 2 to 10-fold change, preferably a 3.5-fold change (increase) in PCT levels is evident in sepsis patients;

for the differentiation between non-infected dyspnea vs. severe sepsis or sepsis with organ dysfunction a 10 to 30-fold change, preferably a 17-fold change (increase) is evident.

In one embodiment of the method described herein the infectious disease is sepsis, severe sepsis and/or septic shock. In one embodiment of the invention the disease to be diagnosed is infection with or without organ dysfunction and/or with or without shock.

In one embodiment of the method described herein the systemic inflammatory condition without an infection is systemic inflammatory response syndrome (SIRS) without infection, such as without an infection by a pathogenic agent or (micro) organism.

In one embodiment of the method described herein determining a level of MMP-8 or fragment(s) thereof, and optionally additionally determining a level of procalcitonin or fragment(s) thereof, occurs within 72 hours, preferably within 48 hours, more preferably within 24, or 12 hours after symptoms of an infectious disease and/or systemic inflammatory condition occur in the patient.

PCT is known to be induced 4-12 hours after infection and has a half life period of 24-35 hours.

The present method enables a fast and reliable determination of infectious disease, thereby enabling early decision making by a medical practitioner for an appropriate treatment. The present invention is therefore particularly relevant for diagnostics in the emergency unit or intensive care setting.

In one embodiment of the method described herein the subject exhibits symptoms of infectious disease, of systemic inflammation, is a post-surgery patient and/or suffers from shortness of breath.

Symptoms may relate to fever over 38° C. or below 36° C., increased heart rate above 90 beats per minute, Tachypnea with a respiratory rate of >than 20/min or $PaCO_2$<32 mmHg (4.3 kPa, hyperventilation, a leucocytosis (≥than 12.000/mm$^3$) or a leucopenia (≤4.000/mm$^3$).

For the purpose of addressing differences between the presence and absence of infectious disease in patients with symptoms of systematic inflammation, the symptoms and/or reference levels of MMP-8 in SIRS patients, or in post-operative patients (who often show systematic inflammation post-OP), may be employed.

In some embodiments the invention is directed to identifying the presence or absence of an infection in patients with dyspnea. Shortness of breath, also known as dyspnea, is a feeling like one cannot breathe well enough. Dyspnea is commonly defined as a subjective experience of breathing discomfort that consists of qualitatively distinct sensations that vary in intensity. Distinct sensations include effort or work required to breath, chest tightness, and air hunger (the feeling of not enough oxygen). Dyspnea is a normal symptom of heavy exertion, but becomes pathological if it occurs in unexpected situations or light exertion. In 85% of cases it is due to asthma, pneumonia, cardiac ischemia, interstitial lung disease, congestive heart failure, chronic obstructive pulmonary disease, further infectious diseases, lung embolism, SIRS or a sepsis, or psychogenic causes, such as panic disorder and anxiety.

When faced with a patient with dyspnea, a medical practitioner requires improved means to identify whether an infection is evident. The invention provides a solution to this problem.

In one embodiment of the method described herein the level of MMP-8 or fragment(s) thereof, and optionally the level of procalcitonin or fragment(s) thereof, is indicative of infectious disease severity. Due to the identification of relatively high levels of MMP-8 the disease severity may also be assessed, providing further information to a medical practitioner regarding the most suited method of treatment. Although correlations between MMP-8 and mortality due to sepsis have been previously disclosed in the art, it was entirely unexpected that MMP-8 in combination with PCT would show improved diagnostic and prognostic statements regarding disease severity of infectious diseases, such as by improving prognostic statements of mortality in patients.

In one embodiment of the method described herein the sample is a blood sample or a sample derived from blood, preferably plasma or serum. Samples may also be employed from other sources, although samples derived from blood are preferred.

In one embodiment of the method described herein the level of MMP-8 or fragment(s) thereof is determined by measuring MMP-8 gene expression, preferably by detecting of MMP-8-encoding RNA or corresponding nucleic acid molecules. As demonstrated in the examples below, the expression levels of MMP-8 encoding RNA can be employed in order to determine the levels of MMP-8 or fragments thereof in a sample.

In one embodiment of the method described herein measuring MMP-8 gene expression comprises a quantitative nucleic acid amplification reaction such as the polymerase chain reaction, preferably real-time PCR (RT-PCR) or digital droplet PCR (ddPCR; a next generation quantitative PCR which offers similar or greater precision and reproducibility than qRT-PCR) employing detection of cDNA corresponding to MMP-8 encoding mRNA. Appropriate primers and/or probes can be developed using the knowledge of a skilled person based on the genome annotation information and on the identified mRNA molecules coding for various forms of MMP-8.

In one embodiment of the method described herein the level of MMP-8 or fragment(s) thereof is determined by measuring MMP-8 protein.

In one embodiment of the method described herein the level of MMP-8 or fragment(s) thereof is determined using a method selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analyzers.

The method according to the present invention can furthermore be embodied as a homogeneous method, wherein the sandwich complexes formed by the antibody/antibodies and the marker, e.g., the MMP-8 protein or a fragment thereof, which is to be detected remains suspended in the liquid phase. In this case it is preferred, that when two antibodies are used, both antibodies are labelled with parts of a detection system, which leads to generation of a signal or triggering of a signal if both antibodies are integrated into a single sandwich.

Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733 A, EP-B1 0 180 492 or EP-B1 0 539 477 and the prior art cited therein. In this way, measurements in which only reaction products comprising both labelling components in a single immune-complex directly in the reaction mixture are detected, become possible.

For example, such technologies are offered under the brand names TRACE® (Time Resolved Amplified Cryptate Emission) or KRYPTOR®, implementing the teachings of the above-cited applications. Therefore, in particular preferred aspects, a diagnostic device is used to carry out the herein provided method. For example, the level of the MMP-8 protein or a fragment thereof, and/or the level of any further marker of the herein provided method is determined. In particular preferred aspects, the diagnostic device is KRYPTOR®.

In a further aspect of the invention MMP-8 levels, optionally in combination with PCT levels, may provide prognostic information of a future adverse event in the health of a subject. Elevated MMP-8 levels are indicative of a future adverse event (such as preferably mortality or organ failure) in patients with symptoms of a systemic inflammatory condition, in particular patients with a relatively low SOFA score (typically between 0-2). This aspect represents a surprising finding, as MMP-8 was not previously known to be used as a prognostic marker for sever adverse events in patients with relatively mild symptoms. As such, elevated MMP-8 levels are of particular importance, regardless of the severity of symtoms of a system inflammatory condition. MMP-8 levels can support clinical practice with regard to escalation or de-escalation of therapeutic measures or can support decision making with regard to a subject's or patient's admission to a medical site or discharge from a medical site.

In one embodiment of the method described herein the method is an immunoassay and wherein the assay is performed in homogeneous phase or in heterogeneous phase.

In one embodiment of the method described herein a first antibody and a second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to said MMP-8 to be detected, a measurable signal which permits detection of the resulting sandwich complexes in the measuring solution is generated.

In one embodiment of the method described herein the labelling system comprises a rare earth cryptate or chelate in combination with a fluorescent or chemiluminescent dye, in particular of the cyanine type.

In one embodiment of the method described herein measuring MMP-8 protein comprises carrying out an immunological assay, wherein said assay comprises:
  Bringing the sample of the subject into contact with a first anti-MMP-8 affinity reagent, preferably an antibody, coupled to a first fluorescent label, and a second anti-MMP-8 affinity reagent, preferably an antibody, coupled to a second fluorescent label,
  Allowing MMP-8 or fragment(s) thereof in said sample to bind to said first and second affinity reagents, thereby forming an antibody-MMP-8 complex, and
  Detecting the first and second fluorescent labels, wherein the fluorescent properties of one or more of said first and/or second fluorescent labels is altered upon binding of the first and second affinity reagents to MMP-8 in said sample.

In one embodiment of the method described herein measuring MMP-8 protein comprises carrying out an immunological assay, wherein said assay comprises:
  Bringing the sample of the subject into contact with a solid phase-immobilised primary anti-MMP-8 affinity reagent, preferably an antibody immobilized on magnetic beads, allowing MMP-8 or fragment(s) thereof in said sample to bind to said primary affinity reagent forming a solid phase-antibody-MMP-8 complex,
  Bringing the solid phase-antibody-MMP-8 complex into contact with a secondary signal-producing affinity reagent, and
  Detecting bound MMP-8 or fragment(s) thereof via the signal from said secondary affinity reagent.

In one embodiment of the method described herein, the method additionally comprises comparing the determined level of MMP-8 or fragment(s) thereof to a reference level, threshold value and/or a population average corresponding to MMP-8 levels in patients with systemic inflammatory condition without an infection, wherein said comparing is carried out in a computer processor using computer executable code.

The methods of the present invention may in part be computer-implemented. For example, the step of comparing the detected level of a marker, e.g. the MMP-8 protein, with a reference level can be performed in a computer system. In the computer-system, the determined level of the marker(s) can be combined with other marker levels and/or parameters of the subject in order to calculate a score which is indicative for the diagnosis, prognosis, risk assessment and/or risk stratification. For example, the determined values may be entered (either manually by a health professional or automatically from the device(s) in which the respective marker level(s) has/have been determined) into the computer-system. The computer-system can be directly at the point-of-care (e.g. ICU or ED) or it can be at a remote location connected via a computer network (e.g. via the internet, or specialized medical cloud-systems, optionally combinable with other IT-systems or platforms such as hospital information systems (HIS)). Typically, the computer-system will store the values (e.g. marker level or parameters such as age, blood pressure, weight, sex, etc. or clinical scoring systems such as SOFA, qSOFA, BMI etc.) on a computer-readable medium and calculate the score based-on pre-defined and/or pre-stored reference levels or reference values. The resulting score will be displayed and/or printed for the user (typically a health professional such as a physician). Alternatively or in addition, the associated prognosis, diagnosis, assessment, treatment guidance, patient management guidance or stratification will be displayed and/or printed for the user (typically a health professional such as a physician).

In one embodiment of the invention, a software system can be employed, in which a machine learning algorithm is evident, preferably to identify hospitalized patients at risk for sepsis, severe sepsis and septic shock using data from electronic health records (EHRs). A machine learning approach can be trained on a random forest classifier using EHR data (such as labs, biomarker expression, vitals, and demographics) from patients. Machine learning is a type of artificial intelligence that provides computers with the ability to learn complex patterns in data without being explicitly programmed, unlike simpler rule-based systems. Earlier studies have used electronic health record data to trigger alerts to detect clinical deterioration in general. In one embodiment of the invention the processing of MMP-8 levels may be incorporated into appropriate software for comparison to existing data sets, for example MMP-8 levels may also be processed in machine learning software to assist in diagnosing or prognosing infection.

In one embodiment of the method described herein, the method additionally comprises treating the subject according to the outcome of the method, either (A) for an infectious disease, wherein said treating comprises administration of appropriate anti-infectious therapeutic agents, such as anti-bacterial, anti-fungal and/or anti-viral therapeutic agents, or (B) for a systemic inflammatory condition without an infection, without administering anti-infectious therapeutic agents.

In one embodiment of the method described herein the determining of a level of MMP-8 or fragment(s) thereof, and optionally additionally determining a level of procalcitonin or fragment(s) thereof, and subsequently treating the subject occurs within 72 hours, preferably within 48 hours, more preferably within 24, or 12 hours after symptoms of an infectious disease and/or systemic inflammatory condition occur in the patient.

A further aspect of the invention relates to a kit for carrying out the method described herein, comprising:
- detection reagents for determining the level of MMP-8 or fragment(s) thereof, and optionally additionally for determining the level of procalcitonin or fragment(s) thereof, in a sample from a subject, and
- reference data such as a reference level, threshold value and/or a population average corresponding to MMP-8 levels, and optionally procalcitonin levels, in patients with systemic inflammatory condition without an infection, wherein said reference data is preferably stored on a computer readable medium and/or employed in in the form of computer executable code configured for comparing the determined level of MMP-8 or fragment(s) thereof, and optionally additionally the determined level of procalcitonin or fragment(s) thereof, to said reference data.

The detection reagents for determining the level of MMP-8 or fragment(s) thereof, and optionally for determining the level of procalcitonin or fragment(s) thereof, are preferably selected from those necessary to perform the method, for example antibodies directed to MMP-8, suitable labels, such as fluorescent labels, preferably two separate fluorescent labels suitable for application in the KRYPTOR assay, sample collection tubes, or PCR detection reagents, such as probes and/or primers directed to MMP-8-encoding nucleic acids, and suitable means for conducting a PCR, sequencing or microarray assay.

In some embodiments of the invention one or more further markers may be employed in combination with the method described herein in order to potentially improve or confirm the diagnostic statements of the method. Misregulation or altered levels of additional markers over suitable controls provides further indication of the presence of an infection in the context of the present invention.

In some embodiments of the invention the at least one further marker of said subject can be selected from the group consisting of adrenomedullin (ADM), pro-adrenomedullin, histone H2A, histone H2B, histone H3, histone H4, procalcitonin, calcitonin, endothelin-1 (ET-1), arginine vasopressin (AVP), atrial natriuretic peptide (ANP), neutrophil gelatinase-associated lipocalin (NGAL), troponin, brain natriuretic peptide (BNP), c-reactive protein (CRP), pancreatic stone protein (PSP), triggering receptor expressed on myeloid cells 1 (TREM1), interleukin-6 (IL-6), interleukin-1, interleukin-24 (IL-24) other ILs, presepsin (sCD14-ST), lipopolysaccharide binding protein (LBP), alpha-1-antitrypsin, matrix metalloproteinase 2 (MMP2), matrix metalloproteinase 9 (MMP9), matrix metalloproteinase 7 (MMP9), soluble fms-like tyrosine kinase-1 (sFlt-1), placental growth factor (PlGF), chromogranin A, S100A protein, S100B protein and tumor necrosis factor α (TNFα) or a fragment thereof. The at least one further marker of said subject can be selected from the group consisting of NGAL, lipocalin-2 (LCN2), olfactomedin 4 (OLFM4) and proteinase 3 (PRTN3).

In further embodiments of the invention the at least one further marker of said subject can be selected from the group consisting of markers involved in the immunological synapse, preferably selected from HLA-DRA, CD40LG, CD3E, CD28 and ICOS.

In preferred embodiments, the expression of HLA-DRA, CD40LG, CD3E, CD28 and/or ICOS genes is reduced in patients with infectious disease compared to patients with systematic inflammation but without infection. As such, MMP-8 levels (and optionally PCT levels) may be assessed in combination with one or more levels of HLA-DRA, CD40LG, CD3E, CD28 and/or ICOS. The increase in MMP-8 and optionally PCT combined with the decrease of one or more levels of HLA-DRA, CD40LG, CD3E, CD28 and/or ICOS provides further indication of an infectious disease.

In one embodiment, the over-expression of MMP-8 and optionally PCT and depressed expression of immunological synapse genes (HLA-DRA, CD40LG, CD3E, CD28 and ICOS), preferably expressed as an expression ratio, preferably MMP8/HLA-DRA, MMP8/CD40LG, MMP8/CD3E, MMP8/CD28 and/or MMP8/ICOS, is capable of differentiating between patients with infection over patients with systematic inflammation symptoms but no infection.

DETAILED DESCRIPTION OF THE INVENTION

The invention relates to a method for the diagnosis, prognosis, risk assessment, risk stratification, monitoring, therapy guidance and/or therapy control of an infectious disease in a subject, wherein said method comprises determining a level of MMP-8 or a fragment thereof in a sample of said subject and wherein said level of MMP-8 is indicative of the presence or absence of an infectious disease in said subject.

In particular, the invention relates to differentiation between the presence and absence of an infectious disease in patients with symptoms of a systemic inflammatory condition. The level of MMP-8 is indicative of the presence of an infectious disease, and the severity of disease, and is further suitable for identifying those patients with symptoms of a systemic inflammatory condition but without an infectious disease. As is evident from the data presented herein, the presence of an infectious disease can be excluded in patients with symptoms of a systemic inflammatory condition due to the MMP-8 levels determined in the method.

Further, the invention relates to a method for the diagnosis, prognosis, risk assessment, risk stratification, monitoring, therapy guidance and/or therapy control of an infectious disease in a subject, wherein said method comprises determining a level of MMP-8 and a level of procalcitonin and/or fragment(s) thereof in a sample of said subject, and wherein said level of MMP-8 and said level of procalcitonin are indicative of said infectious disease.

The present invention has the following advantages over the conventional methods: the inventive methods and the kits are fast, objective, easy to use and precise for the diagnosis of infectious diseases, in particular for the differentiation of systemic inflammatory conditions with vs. without infection. The methods and kits of the invention relate to markers that are easily measurable in routine methods in hospitals, because the levels of MMP-8 and of PCT can be determined in routinely obtained blood samples or further biological fluids or samples obtained from a subject.

Preferably, matrixmetalloproteinase-8 relates to the human gene with the corresponding NCBI Reference Sequence: NC_000011.10) and the respective gene product or fragments thereof.

The gene encoding MMP-8 can be found at location 11q22.2 in the human genome. The gene has been annotated as MMP8 matrix metallopeptidase 8 [*Homo sapiens* (human)], Gene ID: 4317, at the NCBI. According to the current assembly, the gene is described at NC_000011.10.

This gene encodes member 8 of the matrix metalloproteinase (MMP) family of proteins. These proteins are involved in the breakdown of extracellular matrix in embryonic development, reproduction, and tissue remodelling, as well as in disease processes, such as arthritis and metastasis. Proteolysis at different sites on this protein results in multiple active forms of the enzyme with distinct N-termini. This protein functions in the degradation of type I, II and III collagens. The gene is part of a cluster of MMP genes which localize to chromosome 11q22.3. Alternative splicing results in multiple transcript variants.

MMP-8 protein has been annotated at the UniProtKB database under P22894 (MMP8_HUMAN) as a full length 467 amino acid protein.

Antibodies for the detection of MMP-8 are available to a skilled person. For example, anti-MMP-8 antibodies may be obtained from abcam (Cambridge, MA, USA), for example ab81286, ab53017, ab56303, ab154507.

A number of aliases are known for the MMP8 gene, such as matrix metallopeptidase, matrix metalloproteinase 8 (neutrophil collagenase), matrix metalloproteinase-8, PMNL collagenase, PMNL-CL, MMP-8, CLG1, PMN leukocyte collagenase, neutrophil collagenase, collagenase, EC 3.4.24.34, EC 3.4.24 61, and HNC.

The protein may be identified/determined in various forms and fragments and as the full length protein, wherein fragments such as the signal peptide: aa 1-20, the activation peptide: aa 21-100, and the neutrophil collagenase: aa 101-467 are known. Additional fragments may exist.

A number of sequence variations are known for MMP-8, such as:

Natural variant VAR_025036, position 3, S→C, Corresponds to variant dbSNP: rs17099450,
Natural variant VAR_025037, position 32, T→I, Corresponds to variant dbSNP: rs3765620,
Natural variant VAR_006730, position 87, K→E, Corresponds to variant dbSNP: rs1940475,
Natural variant VAR_025038, position 154, G→E, Corresponds to variant dbSNP: rs35056226,
Natural variant VAR_025039, position 193, D→V, Corresponds to variant dbSNP: rs34428739,
Natural variant VAR_025040, position 246, N→Y, Corresponds to variant dbSNP: rs35243553,
Natural variant VAR_025041, position 436, V→A, Corresponds to variant dbSNP: rs34009635,
Natural variant VAR_025042, position 460, K→T, Corresponds to variant dbSNP: rs35866072.

A skilled person is capable of obtaining or developing means for the identification, measurement, determination and/or quantification of any one of the above MMP-8 molecules, or fragments of variants thereof, according to standard molecular biological practice.

The level of MMP-8 in the sample of the subject can be determined by immunoassays as described herein. As used herein, the level of ribonucleic acid or deoxyribonucleic acids encoding MMP-8 can also be determined.

In one embodiment, the method comprises assessment of parameters or characteristics of systemic inflammatory conditions and/or infectious diseases.

As used herein, a parameter is a characteristic, feature, or measurable factor that can help in defining a particular system. A parameter is an important element for health- and physiology-related assessments, such as a disease/disorder/clinical condition risk, preferably an adverse event. Furthermore, a parameter is defined as a characteristic that is objectively measured and evaluated as an indicator of normal biological processes, pathogenic processes, or pharmacologic responses to a therapeutic intervention.

An exemplary parameter can be selected from the group consisting of Acute Physiology and Chronic Health Evaluation score (APACHE scores I-IV), the simplified acute physiology score (SAPS I-III score), sequential organ failure assessment score (SOFA score), quick sepsis-related Organ Failure Assessment score (qSOFA score), simplified acute physiology score II (SAPSII score), mortality probability model (MPM I-III), multiple organ dysfunction score (MODS), therapeutic intervention scoring system (TISS), nine equivalents of nursing manpower use score (NEMS), World Federation of Neurosurgical Societies (WFNS) grading, and Glasgow Coma Scale (GCS), CURB-65 pneumonia severity score, Pneumonia Severity Index (PSI), age, gender, family history, ethnicity, body weight, body mass index (BMI), cystoscopy report, white blood cell count, imaging methods as such as CT scan, PET imaging or X-ray, blood pressure, heart rate, antihypertensive treatment, liquid intake, wheezing, body temperature, presence of diabetes mellitus and current smoking habits.

Such parameters may additionally be assessed in combination with the method described herein in order to improve assay implementation and diagnostic statements.

According to the present invention MMP-8, and optionally PCT, are employed as markers for infectious disease.

A marker or "biomarker" is defined as a characteristic that can be objectively measured and evaluated as an indicator of normal biological processes, pathogenic processes, or pharmacologic responses to a therapeutic intervention. As used herein, additional terms such as "surrogate", "prognostic marker", "factor" or "biological marker" may be used interchangeably with marker or biomarker and relate to measurable and quantifiable biological markers (e.g. specific enzyme concentration or a fragment thereof, specific hormone concentration or a fragment thereof, or presence of biological substances or a fragment thereof) which serve as indices for health- and physiology-related assessments, such as a disease/disorder/clinical condition risk, preferably an infection. A marker is defined as a characteristic that can be objectively measured and evaluated as an indicator of normal biological processes, pathogenic processes, or pharmacologic responses to a therapeutic intervention. The quantification of the biomarker can be performed by measuring the respective ribonucleic acid, deoxyribonucleic acid or protein. Biomarkers may be measured in a biological sample (as a blood, plasma, serum, urine, or tissue test).

As used herein, "procalcitonin" or "PCT" relates to a peptide spanning amino acid residues 1-116, 2-116, 3-116, or fragments thereof, of the procalcitonin peptide. PCT is a peptide precursor of the hormone calcitonin. Thus the length of procalcitonin fragments is at least 12 amino acids, preferably more than 50 amino acids, more preferably more than 110 amino acids. PCT may comprise post-translational modifications such as glycosylation, liposidation or derivatisation. Procalcitonin is a precursor of calcitonin and katacalcin. Thus, under normal conditions the PCT levels in the circulation are very low (<about 0.05 ng/ml).

The level of PCT in the sample of the subject can be determined by immunoassays as described herein. As used herein, the level of ribonucleic acid or deoxyribonucleic acids encoding "procalcitonin" or "PCT" can also be determined. Methods for the determination of PCT are known to a skilled person, for example by using products obtained from Thermo Fisher Scientific/B.R.A.H.M.S GmbH.

As used herein, "infection" within the scope of the invention means a pathological process caused by the invasion of normally sterile tissue or fluid by pathogenic or potentially pathogenic agents/pathogens, organisms and/or microorganisms, and relates preferably to infection(s) by bacteria, viruses, fungi, and/or parasites. Accordingly, the infection can be a bacterial infection, viral infection, and/or fungal infection. The infection can be a local or systemic infection. For the purposes of the invention, a viral infection may be considered as infection by a microorganism.

Further, the subject suffering from an infection can suffer from more than one source(s) of infection simultaneously. For example, the subject suffering from an infection can suffer from a bacterial infection and viral infection; from a viral infection and fungal infection; from a bacterial and fungal infection, and from a bacterial infection, fungal infection and viral infection, or suffer from a mixed infection comprising one or more of the infections listed herein, including potentially a superinfection, for example one or more bacterial infections in addition to one or more viral infections and/or one or more fungal infections.

As used herein "infectious disease" comprises all diseases or disorders that are associated with bacterial and/or viral and/or fungal infections.

In one embodiment the infection to be detected or to be tested for may be selected from species of *Bordetella*, such as *Bordetella pertussis*, *Borrelia*, such as *Borrelia burgdorferi*, *Brucella*, such as *Brucella abortus*, *Brucella canis*, *Brucella melitensis* or *Brucella suis*, *Campylobacter*, such as *Campylobacter jejuni*, *Chlamydia* and *Chlamydophila*, such as *Chlamydia* pneumonia, *Chlamydia trachomatis*, *Chlamydophila psittaci*, *Clostridium*, such as *Clostridium botulinum*, *Clostridium difficile*, *Clostridium perfringens*, *Clostridium tetani*, *Corynebacterium*, such as *Corynebacterium diphtheria*, *Enterococcus*, such as *Enterococcus faecalis*, *Enterococcus faecium*, *Escherichia*, such as *Escherichia coli*, *Francisella*, such as *Francisella tularensis*, *Haemophilus*, such as *Haemophilus* influenza, *Helicobacter*, such as *Helicobacter pylori*, *Legionella*, such as *Legionella pneumophila*, *Leptospira*, such as *Leptospira interrogans*, *Listeria*, such as *Listeria monocytogenes*, *Mycobacterium*, such as *Mycobacterium leprae*, *Mycobacterium tuberculosis*, *Mycobacterium ulcerans*, *Mycoplasma*, such as *Mycoplasma* pneumonia, *Neisseria*, such as *Neisseria gonorrhoeae*, *Neisseria meningitides*, *Pseudomonas*, such as *Pseudomonas aeruginosa*, *Rickettsia*, such as *Rickettsia rickettsia*, *Salmonella*, such as *Salmonella typhi*, *Salmonella typhimurium*, *Shigella*, such as *Shigella sonnei*, *Staphylococcus*, such as *Staphylococcus aureus*, *Staphylococcus epidermidis*, *Staphylococcus saprophyticus*, *Streptococcus*, such as *Streptococcus agalactiae*, *Streptococcus pneumonia*, *Streptococcus pyogenes*, *Treponema*, such as *Treponema pallidum*, *Vibrio*, such as *Vibrio cholera*, *Yersinia*, such as *Yersinia pestis*, *Yersinia enterocolitica* or *Yersinia pseudotuberculosis*.

Pathogenic fungi are fungi that cause disease in humans or other organisms. *Candida* species are important human pathogens that are best known for causing opportunist infections in immunocompromised hosts (e.g. transplant patients, AIDS sufferers, cancer patients). Infections are difficult to treat and can be very serious: 30-40% of systemic infections result in death. Aspergillosis is another potential fungal pathogen. *Aspergillus* can cause disease in three major ways: through the production of mycotoxins; through induction of allergenic responses; and through localized or systemic infections. With the latter two categories, the immune status of the host is pivotal. The most common pathogenic species are *Aspergillus fumigatus* and *Aspergillus flavus*. *Aspergillus flavus* produces aflatoxin which is both a toxin and a carcinogen and which can potentially contaminate foods. *Aspergillus fumigatus* and *Aspergillus clavatus* can cause disease. *Cryptococcus neoformans* can cause disease in humans. *Cryptococcus neoformans* is the major human and animal pathogen. *Cryptococcus laurentii* and *Cryptococcus albidus* have been known to occasionally cause moderate-to-severe disease in human patients with compromised immunity. *Cryptococcus gattii* is endemic to tropical parts of the continent of Africa and Australia and can cause disease. *Histoplasma capsulatum* can cause histoplasmosis in humans, dogs and cats. *Pneumocystis jirovecii* (or *Pneumocystis carinii*) can cause a form of pneumonia in people with weakened immune systems, such as premature children, the elderly, and AIDS patients. Stachybotrys chartarum or "black mould" can cause respiratory damage and severe headaches.

In one embodiment the infection to be detected or to be tested for may be selected from *Acinetobacter baumannii*, *Klebsiella pneumoniae*, *Acinetobacter lwoffii*, *Listeria* monocyto-genes, *Aeromonas caviae*, *Morganella morganii*, *Aeromonas hydrophila*, *Neisseria gonorrhoeae*, *Aspergillus flavus*, *Neisseria meningitidis*, *Aspergillus nidulans*, *Pasteurella multocida*, *Aspergillus niger*, *Pasteurella pneumotropica*, *Aspergillus terreus*, *Propionibacterium acnes*, *Bacillus anthracis*, *Proteus mirabilis*, *Bacillus cereus*, *Providencia rettgeri*, *Bacillus subtilis*, *Pseudomonas aeruginosa*, *Bacteroides fragilis*, *Salmonella choleraesuis*, *Brucella melitensis*, *Serratia liquefaciens*, *Burkholderia cepacia*, *Serratia marcescens*, *Candida albicans*, *Staphylococcus aureus*, *Candida dubliniensis*, *Staphylococcus epidermidis*, *Candida glabrata*, *Staphylococcus haemolyticus*, *Candida krusei*, *Staphylococcus hominis*, *Candida parapsilosis*, *Staphylococcus saccharolyticus*, *Candida tropicalis*, *Staphylococcus* warn-eri, *Capnocytophaga canimorsus*, *Stenotrophomonas maltophilia*, *Citrobacter braakii*, *Streptococcus agalactiae*, *Citrobacter freundii*, *Streptococcus anginosus*, *Clostridium perfringens*, *Streptococcus bovis*, *Corynebacterium jeikeium*, *Streptococcus constellatus*, *Enterobacter aerogenes*, *Streptococcus dysgalactiae*, *Enterobacter cloacae*, *Streptococcus mutans*, *Enterobacter sakazakii*, *Streptococcus pneumoniae*, *Enterococcus faecalis*, *Streptococcus pyogenes*, *Enterococcus faecium*, *Streptococcus salivarius*, *Escherichia coli*, *Streptococcus sanguinis*, *Shigella* sp., *Streptococcus suis*, *Gemella haemolysans*, *Vibrio vulnificus*, *Gemella morbillorum*, *Yersinia enterocolitica*, *Haemophilus influenzae*, *Yersinia pestis*, *Kingella kingae*, *Yersinia pseudotuberculosis* and; *Klebsiella oxytoca*.

As used herein, the "subject" (or "patient") may be a vertebrate. In the context of the present invention, the term "subject" includes both humans and animals, particularly mammals, and other organisms. Thus, the herein provided methods are applicable to both human and animal subjects.

In one embodiment of the invention the subject to be tested can be a subject that suffers from a disease or medical condition, and wherein said disease or medical condition is selected from the group consisting of cardiovascular disease, diabetes mellitus, malignancy, respiratory disease, liver disease, renal disease immunodepression, an inflammatory response related to infective and non-infective aetiologies, systemic inflammatory response syndrome (SIRS), an infection with or without organ dysfunction, sepsis, severe sepsis, and/or septic shock.

The subject described herein can also be a pre- or post-surgical patient, a trauma patient, such as accident patients, burn patients, patients with open lesions, a patient suffering shortness of breath or a patient with non-specific complaints.

The subject described herein can be at the emergency department or intensive care unit, or in other point of care settings, such as in an emergency transporter, such as an ambulance, or at a general practitioner, who is confronted with a patient with said symptoms.

Despite the underlying pathology, the patient is to be defined by at least one symptom of a systemic inflammatory condition, such as a SIRS. This patient group is of particular interest, in order to determine whether an infectious disease is present.

"SIRS" in the context of the invention is a systemic inflammatory response syndrome with no signs of infection. It includes, but is not limited to more than one of the following clinical manifestations: (1) a body temperature greater than 38° C. or less than 36° C.; (2) a heart rate greater than 90 beats per minute; (3) tachypnea, manifested by a respiratory rate greater than 20 breaths per minute, or hyperventilation, as indicated by a $PaCO_2$ of less than 32 mm Hg; and (4) an alteration in the white blood cell count such as a count greater than 12,000/mm$^3$, a count less than 4,000/mm$^3$, or the presence of more than 10% immature neutrophils (Bone et al., CHEST 101 (6): 1644-55, 1992).

Particularly, the subject suffers from sepsis. More particularly, the subject may suffer from severe sepsis and/or septic shock.

"Sepsis" in the context of the invention refers to a systemic response to infection. Alternatively, sepsis may be seen as the combination of SIRS with a confirmed infectious process or an infection. Sepsis may be characterized as clinical syndrome defined by the presence of both infection and a systemic inflammatory response (Levy M M et al. 2001 SCCM/ESICM/ACCP/ATS/SIS International sepsis Definitions Conference. Crit Care Med. 2003 April; 31 (4): 1250-6). The term "sepsis" used herein includes, but is not limited to, sepsis, severe sepsis, septic shock.

The term sepsis may alternatively be defined as life-threatening organ dysfunction caused by a dysregulated host response to infection. For clinical operationalization, organ dysfunction can preferably be represented by an increase in the Sequential Organ Failure Assessment (SOFA) score of 2 points or more, which is associated with an in-hospital mortality greater than 10%. Septic shock may be defined as a subset of sepsis in which particularly profound circulatory, cellular, and metabolic abnormalities are associated with a greater risk of mortality than with sepsis alone. Patients with septic shock can be clinically identified by a vasopressor requirement to maintain a mean arterial pressure of 65 mm Hg or greater and serum lactate level greater than 2 mmol/L (>18 mg/dL) in the absence of hypovolemia.

Severe sepsis in refers to sepsis associated with organ dysfunction, hypo perfusion abnormality, or sepsis-induced hypotension. Hypo perfusion abnormalities include lactic acidosis, oliguria and acute alteration of mental status. Sepsis-induced hypotension is defined by the presence of a systolic blood pressure of less than about 90 mm Hg or its reduction by about 40 mm Hg or more from baseline in the absence of other causes for hypotension (e.g. cardiogenic shock). Septic shock is defined as severe sepsis with sepsis-induced hypotension persisting despite adequate fluid resuscitation, along with the presence of hypo perfusion abnormalities or organ dysfunction (Bone et al., CHEST 101 (6): 1644-55, 1992).

The term "sepsis" used herein relates to all possible stages in the development of sepsis.

The "sample" of the invention refers to any biological sample taken from an individual. The biological sample may be blood, plasma, saliva, serum, sputum, urine, cerebral spinal fluid, cells, a cellular extract, a tissue sample, a tissue biopsy, a stool sample and the like.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood), for example for at least 15 minutes at 2000 to 3000 g.

"Serum" in the context of the present invention is the liquid fraction of whole blood that is collected after the blood is allowed to clot. When coagulated blood (clotted blood) is centrifuged serum can be obtained as supernatant.

As used herein, "urine" is a liquid product of the body secreted by the kidneys through a process called urination (or micturition) and excreted through the urethra.

In some embodiments the invention relates to detection of MMP-8 encoding nucleic acids. The nucleic acid target (genome, gene or gene fragment (e.g., a restriction fragment) of any given marker) may be in a purified, un-purified form or in an isolated form. The nucleic acid target may be contained within a sample including for example, a biological specimen obtained from a patient, for example a blood, serum or plasma sample. In accordance with the present invention, the sample may be obtained from patient having or suspected of having an infection.

MMP-8 encoding nucleic acids may be determined using nucleic acid sequencing approaches, for example next generation sequencing, such as employing ABI SOLID, Illumina Genome Analyzer, Roche/454 GS FLX, and the like, One preferred embodiment relates to real time PCR (RT-PCR) or quantitative RT-PCR (qRT-PCR), as it allows the quantification of the amplified target in real-time. The term "real-time PCR" is intended to mean any amplification technique which makes it possible to monitor the progress of an ongoing amplification reaction as it occurs (i.e. in real time). Data is therefore collected during the exponential phase of the PCR reaction, rather than at the end point as in conventional PCR. Measuring the kinetics of the reaction in the early phases of PCR provides distinct advantages over traditional PCR detection. In real-time PCR, reactions are characterized by the point in time during cycling when amplification of a target is first detected rather than the amount of target accumulated after a fixed number of cycles. The higher the starting copy number of the nucleic acid target, the sooner a significant increase in fluorescence is observed. Traditional PCR methods may also be applied, and use separation methods, such as agarose gels, for detection of PCR amplification at the final phase of or end-point of the PCR reaction. For qRT-PCR no post-PCR processing of the unknown DNA sample is necessary as the quantification occurs in real-time during the reaction. Furthermore, an increase in reporter fluorescent signal is directly proportional to the number of amplicons generated.

As the method was designed to use similar experimental conditions, the PCR amplification for each multiplex can be performed using the same thermal cycling profile thereby allowing the amplification of all the nucleic acid targets at the same time in a single apparatus (e.g., thermocycler).

Although nucleic acid amplification is often performed by PCR or RT-PCR, other methods exist. Non-limiting examples of such method include quantitative polymerase chain reaction (Q-PCR), digital droplet PCR (ddPCR), ligase chain reaction (LCR), transcription-mediated amplification (TMA), self-sustained sequence replication (3SR), nucleic acid sequence-based amplification (NASBA), strand displacement amplification (SDA), recombinase polymerase amplification (RPA), loop-mediated isothermal amplification (LAMP), helicase-dependent amplification (HDA), helicase-dependent isothermal DNA amplification (tHDA), branched DNA (bDNA), cycling probe technology (CPT), solid phase amplification (SPA), rolling circle amplification technology (RCA), real-time RCA, solid phase RCA, RCA coupled with molecular padlock probe (MPP/RCA), aptamer based RCA (aptamer-RCA), anchored SDA, primer extension preamplification (PEP), degenerate oligonucleotide primed PCR (DOP-PCR), sequence-independent single primer amplification (SISPA), linker-adaptor PCR, nuclease dependent signal amplification (NDSA), ramification amplification (RAM), multiple displacement amplification (MDA), real-time RAM, and whole genome amplification (WGA) (Westin, L. et al., 2000, Nat. Biotechnol. 18:199-204; Notomi, T. et al., 2000, Nucleic Acids Res. 28: e63; Vincent, M. et al., 2004, EMBO reports 5:795-800; Piepenburg, O. et al., 2006, PLOS Biology 4: E204; Yi, J. et al., 2006, Nucleic Acids Res. 34: e81; Zhang, D. et al., 2006, Clin. Chim. Acta 363:61-70; Mccarthy, E. L. et al., 2007, Biosens. Biotechnol. 22:126-1244; Zhou, L. et al., 2007, Anal. Chem. 79:7492-7500; Coskun, S. and Alsmadi, O., 2007, Prenat. Diagn. 27:297-302; Biagini, P. et al., 2007, J. Gen. Virol. 88:2629-2701; Gill, P. et al., 2007, Diagn. Microbiol. Infect. Dis. 59:243-249; Lasken, R. S. and Egholm, M., 2003, Trends Biotech. 21:531-535).

PCR reactions may be performed in mixture containing template genomic DNA preparation obtained for each of the microbial species and diluted at the desired concentration, a buffer suitable for amplification using desired polymerases, primers at a predetermined concentration, dinucleotide triphosphate (dNTPs) mix and DNA polymerase. In order to minimize nucleic acid contamination levels from reagents and solutions, stock solutions may be filtered and solutions may be sterilized and exposed to UV (e.g., using a Spectrolinker™ XL-1000 (Spectronics Corp.) between 9999 and 40 000 µJ/cm2). UV exposure may be adjusted as described in patent application WO 03087402A1. An internal control designed to monitor amplification efficiency may be added in the multiplex assay(s). Amplification runs may also include no template (negative) control reactions. Amplification may be performed in any thermal cycler. The amplification conditions typically include a step of denaturation of the nucleic acid where suitable denaturation conditions are used, a step of hybridization (annealing) where suitable hybridization conditions are used, a step of extension where suitable extension conditions by the polymerase are used. The amplicons were typically melted between a range of 60° to 95° C. As known by the person skilled in the art, reaction chemistry and cycling conditions may vary and may be optimized for different PCR reagents combinations and thermocycling devices.

It should also be understood herein that the scope of the invention is not limited to a specific detection technology. Classically, detection of amplified nucleic acids is performed by standard ethidium bromide-stained agarose gel electrophoresis. Briefly, 10 µL of the amplification mixture are resolved by electrophoresis in a 2% agarose gel containing 0.25 µg/mL of ethidium bromide. The amplicons are then visualized under a UV transilluminator. Amplicon size is estimated by comparison with a molecular weight ladder. It is however clear that other method for the detection of specific amplification products, which may be faster and more practical for routine diagnosis, may be used. Such methods may be based on the detection of fluorescence after or during amplification.

One simple method for monitoring amplified DNA is to measure its rate of formation by measuring the increase in fluorescence of intercalating agents such as ethidium bromide or SYBR® Green I (Molecular Probes). If a more specific detection is required, fluorescence-based technologies can monitor the appearance of a specific product during the nucleic acid amplification reaction. The use of dual-labelled fluorogenic probes such as in the TaqMan™ system (Applied Biosystems) which utilizes the 5'-3' exonuclease activity of the Taq polymerase is a good example (Livak K. J. et al., 1995, PCR Methods Appl. 4:357-362). TaqMan™ probes are used during amplification and this "real-time" detection is performed in a closed vessel hence eliminating post-PCR sample handling and consequently preventing the risk of amplicon carryover.

Several other fluorescence-based detection methods can be performed in real-time. Examples of such fluorescence-based methods include the use of adjacent hybridization probes (Wittwer, C. T. et al., 1997, BioTechniques 22:130-138), molecular beacon probes (Tyagi S. and Kramer F. R., 1996, Nat. Biotech. 14:303-308) and scorpion probes (Whitcombe, D. et al., 1999, Nat. Biotechnol. 17:804-807). Adjacent hybridization probes are designed to be internal to the amplification primers. The 3' end of one probe is labelled with a donor fluorophore while the 5' end of an adjacent probe is labelled with an acceptor fluorophore. When the two probes are specifically hybridized in closed proximity (spaced by 1 to 5 nucleotides) the donor fluorophore which has been excited by an external light source emits light that is absorbed by a second acceptor that emit more fluorescence and yields a fluorescence resonance energy transfer (FRET) signal. Molecular beacon probes possess a stem-and-loop structure where the loop is the probe and at the bottom of the stem a fluorescent moiety is at one end while a quenching moiety is at the other end. The molecular beacons undergo a fluorogenic conformational change when they hybridize to their targets hence separating the fluorophore from its quencher. The FRET principle has been used for real-time detection of PCR amplicons in an air thermal cycler equipped with a built-in fluorometer (Wittwer, C. T. et al., 1997, BioTechniques 22:130-138). Apparatus for real-time detection of PCR amplicons are capable of rapid PCR cycling combined with either fluorescent intercalating agents such as SYBR® Green I or FRET detection. Methods based on the detection of fluorescence are particularly promising for utilization in routine diagnosis as they are very simple, rapid and quantitative.

A melting curve analysis may also be used as an alternative to fluorescent techniques. Melting curve analysis is an assessment of the dissociation-characteristics of double-stranded DNA during heating. As the temperature is raised, the double strand begins to dissociate leading to a rise in the absorbance intensity, hyperchromicity. The information gathered can be used to infer the presence and identity of sequence, for example single-nucleotide polymorphisms (SNP). This is due to the fact that G-C base pairing have 3 hydrogen bonds between them while A-T base pairs have only 2. DNA with a higher G-C content, whether because of its source or, as previously mentioned, because of SNPs, will have a higher melting temperature than DNA with a higher A-T content.

Melting curve analysis, for example of PCR products via SYBR Green, other double-strand specific dyes, or probe-based melting curve analysis has become common. The probe-based technique is sensitive enough to detect single-nucleotide polymorphisms (SNP) and can distinguish between homozygous wildtype, heterozygous and homozygous mutant alleles by virtue of the dissociation patterns produced. Without probes, amplicon melting (melting and analysis of the entire PCR product) was not generally successful at finding single base variants through melting profiles. With higher resolution instruments and advanced dyes, amplicon melting analysis of one base variants is now possible with several commercially available instruments. For example: Applied Biosystems 7500 Fast System and the 7900HT Fast Real-Time PCR System, Idaho Technology's LightScanner (the first plate-based high resolution melting device), Qiagen's Rotor-Gene instruments, and Roche's LightCycler 480 instruments.

Droplet Digital PCR technology is a digital PCR method utilizing a water-oil emulsion droplet system. Droplets are formed in a water-oil emulsion to form the partitions that separate the template DNA molecules. The droplets serve essentially the same function as individual test tubes or wells in a plate in which the PCR reaction takes place, albeit in a much smaller format. The massive sample partitioning is a key aspect of the ddPCR technique. The Droplet Digital PCR System partitions nucleic acid samples into thousands of nanoliter-sized droplets, and PCR amplification is carried out within each droplet. This technique has a smaller sample requirement than other commercially available digital PCR systems, reducing cost and preserving precious samples.

As used herein, the term "hybridization" refers to the binding of two complementary strands of nucleic acid to form a double-stranded molecule (hybrid).

Methods of determining MMP-8 protein are intended in the present invention. By way of example, a method may be employed selected from the group consisting of mass spectrometry (MS), luminescence immunoassay (LIA), radioimmunoassay (RIA), chemiluminescence- and fluorescence-immunoassays, enzyme immunoassay (EIA), enzyme-linked immunoassays (ELISA), luminescence-based bead arrays, magnetic beads based arrays, protein microarray assays, rapid test formats such as for instance immunochromatographic strip tests, rare cryptate assay, and automated systems/analyzers.

Determination of MMP-8 based on antibody recognition is a preferred embodiment of the invention. As used herein, the term, "antibody" refers to immunoglobulin molecules and immunologically active portions of immunoglobulin (Ig) molecules, i.e., molecules that contain an antigen binding site that specifically binds (immuno reacts with) an antigen. According to the invention, the antibodies may be monoclonal as well as polyclonal antibodies. Particularly, antibodies that are specifically binding to MMP-8 or fragments thereof and optionally that bind specifically to PCT are used.

An antibody is considered to be specific, if its affinity towards the molecule of interest, e.g. MMP-8, or the fragment thereof is at least 50-fold higher, preferably 100-fold higher, most preferably at least 1000-fold higher than towards other molecules comprised in a sample containing the molecule of interest. It is well known in the art how to develop and to select antibodies with a given specificity. In the context of the invention, monoclonal antibodies are preferred. The antibody or the antibody binding fragment binds specifically to the herein defined markers or fragments thereof. In particular, the antibody or the antibody binding fragment binds to the herein defined peptides of MMP-8 protein.

Further, an antibody or an antibody binding fragment is used in the methods and kits of the invention that binds specifically to MMP-8 or PCT. Exemplary immunoassays can be luminescence immunoassay (LIA), radioimmunoassay (RIA), chemiluminescence- and fluorescence-immunoassays, enzyme immunoassay (EIA), enzyme-linked immunoassays (ELISA), luminescence-based bead arrays, magnetic beads based arrays, protein microarray assays, rapid test formats, rare cryptate assay. Further, assays suitable for point-of-care testing and rapid test formats such as for instance immune-chromatographic strip tests can be employed. Automated immunoassays are also intended, such as the KRYPTOR assay. Combinations between immune assays and nucleic acid based assays are also envisaged as falling within the scope of the present invention.

Alternatively, instead of antibodies, other capture molecules or molecular scaffolds that specifically and/or selectively recognize MMP-8 may be encompassed by the scope of the present invention. Herein, the term "capture molecules" or "molecular scaffolds" comprises molecules which may be used to bind target molecules or molecules of interest, i.e. analytes (e.g. MMP-8 and PCT), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may, for instance, be mediated by ionic, van-der-Waals, pi-pi, sigma-pi, hydrophobic or hydrogen bond interactions or a combination of two or more of the aforementioned interactions or covalent interactions between the capture molecules or molecular scaffold and the target molecules or molecules of interest. In the context of the present invention, capture molecules or molecular scaffolds may for instance be selected from the group consisting of a nucleic acid molecule, a carbohydrate molecule, a PNA molecule, a protein, a peptide and a glycoprotein. Capture molecules or molecular scaffolds include, for example, aptamers, DARpins (designed ankyrin repeat proteins). Affimers and the like are included.

In a preferred embodiment, the method is executed as heterogeneous sandwich immunoassay, wherein one of the antibodies is immobilized on an arbitrarily chosen solid phase, for example, the walls of coated test tubes (e.g. polystyrol test tubes; coated tubes; CT) or microtiter plates, for example composed of polystyrol, or to particles, such as for instance magnetic particles, whereby the other antibody has a group resembling a detectable label or enabling for selective attachment to a label, and which serves the detection of the formed sandwich structures. A temporarily delayed or subsequent immobilization using suitable solid phases is also possible.

The method according to the present invention can furthermore be embodied as a homogeneous method, wherein the sandwich complexes formed by the antibody/antibodies and the marker, e.g., the MMP-8 or the PCT or a fragment thereof, which is to be detected remains suspended in the liquid phase. In this case it is preferred, that when two antibodies are used, both antibodies are labeled with parts of a detection system, which leads to generation of a signal or triggering of a signal if both antibodies are integrated into a single sandwich. Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733, EP0180492 or EP0539477 and the prior art cited therein. In this way, measurements in which only reaction products comprising both labeling components in a single immune-complex directly in the reaction mixture are detected, become possible. For example, such technologies are offered under the brand names TRACE® (Time Resolved Amplified Cryptate Emission) or KRYPTOR®, implementing the teachings of the above-cited applications. Therefore, in particular preferred aspects, a diagnostic device is used to carry out the herein provided method. For example, the level of MMP-8 and/or PCT or a fragment thereof, and/or the level of any further marker of the herein provided method is determined. In particular preferred aspects, the diagnostic device is KRYPTOR®.

The level of the marker, e.g. the MMP-8 or PCT, can also be determined by a mass spectrometric (MS) based analysis as described in the appended examples. Such a method may comprise detecting the presence, amount or concentration of one or more modified or unmodified fragment peptides of e.g. MMP-8 or the PCT in said biological sample or a protein digest (e.g. tryptic digest) from said sample, and optionally separating the sample with chromatographic methods, and subjecting the prepared and optionally separated sample to MS analysis. For example, selected reaction monitoring (SRM), multiple reaction monitoring (MRM) or parallel reaction monitoring (PRM) mass spectrometry may be used in the MS analysis, particularly to determine the amounts of MMP-8.

Herein, the term "mass spectrometry" or "MS" refers to an analytical technique to identify compounds by their mass. In order to enhance the mass resolving and mass determining capabilities of mass spectrometry, the samples can be processed prior to MS analysis. Accordingly, the invention relates to MS detection methods that can be combined with immuno-enrichment technologies, methods related to sample preparation and/or chromatographic methods, preferably with liquid chromatography (LC), more preferably with high performance liquid chromatography (HPLC) or ultra high performance liquid chromatography (UHPLC). Sample preparation methods comprise techniques for lysis, fractionation, digestion of the sample into peptides, depletion, enrichment, dialysis, desalting, alkylation and/or peptide reduction. However, these steps are optional. The selective detection of analyte ions may be conducted with tandem mass spectrometry (MS/MS). Tandem mass spectrometry is characterized by mass selection step (as used herein, the term "mass selection" denotes isolation of ions having a specified m/z or narrow range of m/z's), followed by fragmentation of the selected ions and mass analysis of the resultant product (fragment) ions.

The skilled person is aware how quantify the level of a marker in the sample by mass spectrometric methods. For example, relative quantification "rSRM" or absolute quantification can be employed as described above.

Moreover, the levels (including reference levels) can be determined by mass spectrometric based methods, such as methods determining the relative quantification or determining the absolute quantification of the protein or fragment thereof of interest.

As used herein, "diagnosis" in the context of the present invention relates to the recognition and (early) detection of infections and may also comprise differential diagnosis. Also the assessment of the severity of the infection may be encompassed by the term "diagnosis".

"Prognosis" relates to the prediction of an outcome or a specific risk for a subject to suffer from an infection. This may also include an estimation of the chance of recovery or the chance of an adverse outcome for said subject.

The methods of the invention may also be used for monitoring. "Monitoring" relates to keeping track of an already diagnosed infection, infection related disorder or complication or risk, e.g. to analyse the progression of the disease or the influence of a particular treatment on the progression of the infection or infection related disorder or complication or risk.

The term "therapy control" in the context of the present invention refers to the monitoring and/or adjustment of a therapeutic treatment of said subject.

In the present invention, the terms "risk assessment" and "risk stratification" relate to the grouping of subjects into different risk groups according to their further prognosis. Risk assessment also relates to stratification for applying preventive and/or therapeutic measures.

As used herein, the term "therapy guidance" refers to application of certain therapies or medical interventions based on the value of one or more biomarkers and/or clinical parameter and/or clinical scores.

The invention further relates to kits, the use of the kits and methods wherein such kits are used. The invention relates to kits for carrying out the herein above and below provided methods. The herein provided definitions, e.g. provided in relation to the methods, also apply to the kits of the invention. In particular, the invention relates to kits for the diagnosis, prognosis, risk assessment, risk stratification, monitoring, therapy guidance and/or therapy control of an infection in said subject, wherein said kit comprises (i)—detection reagents for determining said level of MMP-8 in said sample of said subject, and
  reference data including said reference level of MMP-8, and wherein an increased level of said MMP-8 in said sample of said subject as compared to said reference level of at MMP-8 is indicative of an infection in said subject; and optionally (ii)—detection reagents for determining said level of PCT in said sample of said subject, and
  reference data including said reference level of PCT, and
  wherein an increased level of said PCT in said sample of said subject as compared to said reference level of PCT is indicative of an infection in said subject.

As used herein, "reference data" comprise reference level(s) of MMP-8 and/or of PCT. The levels of MMP-8 and/or of PCT in the sample of the subject can be compared to the reference levels comprised in the reference data of the kit. An increased level of the marker(s) determined is indicative of infection. The reference levels are herein described above and are exemplified also in the appended examples. The reference data can also include a reference sample to which the level of MMP-8 and/or of PCT is compared to. The reference data can also include an instruction manual how to use the kits of the invention.

The kit may additionally comprise items useful for obtaining a sample, such as a blood sample, for example the kit may comprise a container, wherein said container comprises a device for attachment of said container to a cannula or syringe, is a syringe suitable for blood isolation, exhibits an internal pressure less than atmospheric pressure, such as is suitable for drawing a pre-determined volume of sample into said container, and/or comprises additionally detergents, chaotropic salts, ribonuclease inhibitors, chelating agents, such as guanidinium isothiocyanate, guanidinium hydrochloride, sodium dodecylsulfate, polyoxyethylene sorbitan monolaurate, RNAse inhibitor proteins, and mixtures thereof, and/or A filter system containing nitro-cellulose, silica matrix, ferromagnetic spheres, a cup retrieve spill over, trehalose, fructose, lactose, mannose, poly-ethylenglycol, glycerol, EDTA, TRIS, limonene, xylene, benzoyl, phenol, mineral oil, anilin, pyrol, citrate, and mixtures thereof.

As used herein, the "detection reagent" or the like are reagents that are suitable to determine the herein described marker(s), e.g. of MMP-8 and/or of PCT. Such exemplary detection reagents are, for example, ligands, e.g. antibodies or fragments thereof, which specifically bind to the peptide or epitopes of the herein described marker(s). Such ligands might be used in immunoassays as described above. Further reagents that are employed in the immunoassays to determine the level of the marker(s) may also be comprised in the kit and are herein considered as detection reagents. Detection reagents can also relate to reagents that are employed to detect the markers or fragments thereof by MS based methods. Such detection reagent can thus also be reagents, e.g. enzymes, chemicals, buffers, etc, that are used to prepare the sample for the MS analysis. A mass spectrometer can also be considered as a detection reagent. Detection reagents according to the invention can also be calibration solution(s), e.g. which can be employed to determine and compare the level of the marker(s).

The kit may be suitable for the PCR-based determination of MMP-8 and optionally other biomarkers described herein. For example, a PCR kit may comprise one or more oligonucleotides for amplifying a nucleic acid encoding a marker as described herein and/or an oligonucleotide set for amplifying multiple nucleic acid molecules encoding markers as described herein, and amplification reagents, such as one or more fluorescent labels, dNTPs, buffers and/or enzymes. The kit as described herein may be understood as a combination of components, preferably contained however within separate containers, but within close proximity to one another. The kit may be provided with or without specific PCR reagents. In one embodiment the kit may encompass all those reagents necessary for carrying out an RT-PCR, or ddPCR, or other appropriate PCR method, including preferably pre-labelled probes, buffers, enzymes, dNTPs and any further reagents.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having an infection and "disease" populations, e.g. subjects having an infection. For any particular marker (like MMP-8), a distribution of marker levels for subjects with and without a disease/condition will likely overlap. Under such conditions, a test does not absolutely distinguish normal from disease with 100% accuracy, and the area of overlap might indicate where the test cannot distinguish normal from disease. A threshold is selected, below which the test is considered to be abnormal and above which the test is considered to be normal or below or above which the test indicates a specific condition, e.g. infection. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art; see, e.g., Hanley et al. 1982. Radiology 143:29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

Treatment may be conducted in combination with the diagnostic assay described herein. By way of example, antibiotics may be administered if an infection is determined. Antibiotics according to the present invention also encompass potentially the anti-fungal or anti-viral compounds used to treat a diagnosed infection or sepsis. The antibiotics commonly applied in the treatment of any given infection, as separated into the classes of pathogen are:

Gram positive coverage: penicillins, (ampicillin, amoxicillin), penicillinase resistant, (dicloxacillin, oxacillin), cephalosporins (1st and 2nd generation), macrolides (erythromycin, clarithromycin, azithromycin), quinolones (gatifloxacin, moxifloxacin, levofloxacin), vancomycin, sulfonamide/trimethoprim, clindamycin, tetracyclines, chloramphenicol, linezolid, synercid.

Gram negative coverage: Broad spectrum penicillins (ticarcillin, clavulanate, piperacillin, tazobactam), cephalosporins (2nd, 3rd, and 4th generation), aminoglycosides, macrolides, azithromycin, quinolones (ciprofloxacin), monobactams (azetreonam), sulfona-mide/trimethoprim, carbapenems (imipenem), chloramphenicol.

*Pseudomonas* coverage: ciprofloxacin, aminoglycosides, some 3rd generation cephalosporins, 4th generation cephalosporins, broad spectrum penicillins, carbapenems.

Fungal treatments: amphotericin B, fluconazole and other azoles, itraconazole, voriconazole, posaconazole, ravuconazole, echinocandins, Flucytosine, sordarins, chitin synthetase inhibitors, topoisomerase inhibitors, lipopeptides, pradimycins, liposomal nystatin, voriconazole.

Anti-viral treatments: abacavir, acyclovir (Aciclovir), adefovir, amantadine, amprenavir (agenerase), ampligen, arbidol, atazanavir, atripla, balavir, cidofovir, combivir, dolutegravir, darunavir, delavirdine, didanosine, docosanol, edoxudine, efavirenz, emtricitabine, enfuvirtide, entecavir, ecoliever, famciclovir, fixed dose combination (antiretroviral), fomivirsen, fosamprenavir, foscarnet, fosfonet, fusion inhibitor, ganciclovir, ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, methisazone, nelfinavir, nevirapine, nexavir, nitazoxanide, nucleoside analogues, novir, oseltamivir (tamiflu), peginterferon alfa-2a, penciclovir, eramivir, pleconaril, podophyllotoxin, protease inhibitor (pharmacology), raltegravir, reverse transcriptase inhibitor, ribavirin, rimantadine, ritonavir, pyramidine, saquinavir, sofosbuvir, stavudine, synergistic enhancer (antiretroviral), telaprevir, tenofovir, tenofovir disoproxil, tipranavir, trifluridine, trizivir, tromantadine, truvada, valaciclovir (valtrex), valganciclovir, vicriviroc, vidarabine, viramidine, zalcitabine, zanamivir (relenza), zidovudine.

Accordingly, the invention comprises the administration of an antibiotic suitable for treatment on the basis of the information obtained by the method described herein.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

Thus, the terms "comprising"/"including"/"having" mean that any further component (or likewise features, integers, steps and the like) can/may be present. The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

The present invention is further described by reference to the following non-limiting figures and examples.

FIGURES

FIG. 1: MMP-8 levels as assessed by droplet digital PCR using predesigned TaqMan® Assay Primer/Probe Sets (FAM labelled MGB probes, Thermo Fisher/Scientific-Life Technologies, Waltham, MA, USA). MMP-8 levels in different patient groups are shown, expressed as (copies/ng) log. Also shown in the table in FIG. 1c are AUROC and p values in SIRS and in sepsis patient groups for MMP-8, and MMP-8 and PCT.

Figure 2:
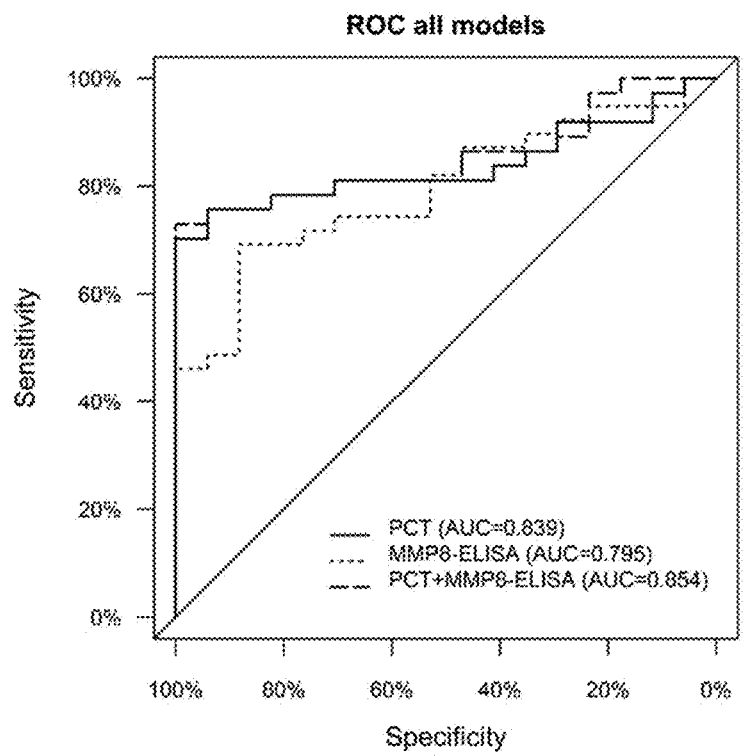

FIG. 2: ROC curves for SIRS vs. Sepsis differentiation of PCT, MMP8 and the combination of both markers, when measured using ELISA. Combining PCT with MMP8 is also shown.

Figure 3:
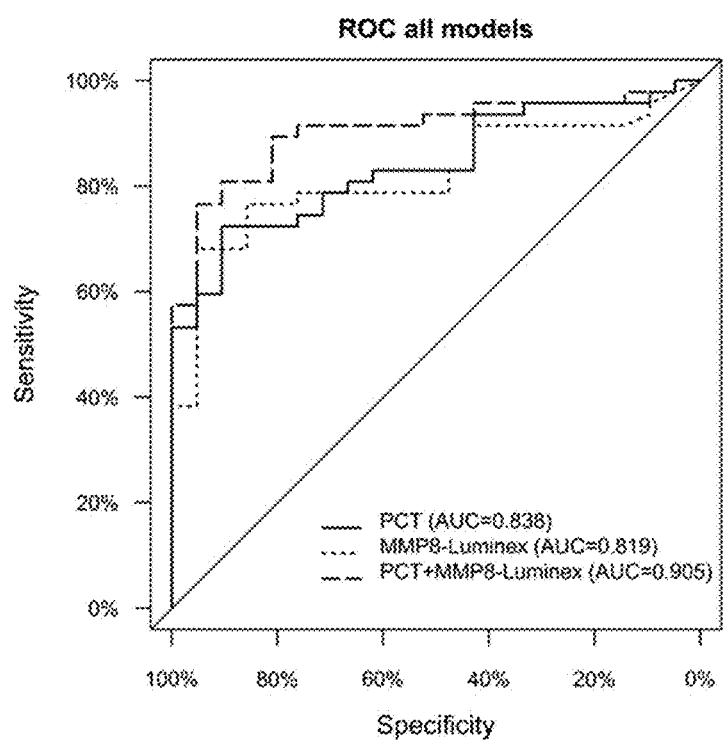

FIG. 3: ROC curves for dyspnea vs. sepsis differentiation of PCT, MMP8 measured by MagPix and the combination of both markers.

Figure 4:
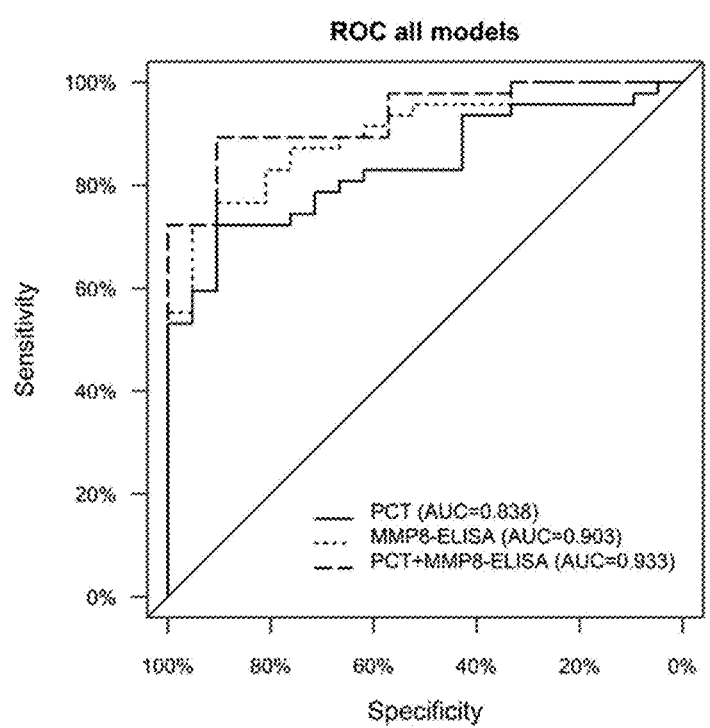

FIG. 4: ROC curves for dyspnea vs. sepsis differentiation of PCT, MMP8 measured by ELISA and the combination of both markers. Combining PCT+MMP8 significantly increases the AUC and thereby the ability to differentiate dyspnea and sepsis patients.

EXAMPLES

Example 1

Patients with Sepsis Show Increased Levels of MMP-8 Over Control Groups with SIRS
Patients:

158 adult patients (>18 years old) were assessed in the study. 57 uninfected SIRS patients were recruited as control group with no sepsis. In addition, 18 blood donors of similar age of the patients were recruited as healthy controls. 83 patients were diagnosed as septic patients (according to the definition proposed by the American College of Chest Physicians/Society of Critical Care Medicine Consensus Conference), whereby of these 44 patients suffered a septic shock.

Written informed consent was obtained directly from all patients, or their legal representative, before enrolment. Scientific and ethical approval of the study protocol was obtained from the respective scientific committees for clinical research of the participant hospitals. Standard cultures in biological samples guided by the presumptive source of the septic insult were performed to assess the presence of bacterial and fungal infection. Potentially contaminant microorganisms were not considered.
ddPCR mRNA Extraction and Quality Evaluation:

A sample of 2.5 mL of blood was collected by using PaxGene (BD) venous blood vacuum collection tubes in the first 12 hours following diagnosis of sepsis or in the first 12 hours following surgery in the case of the surgical controls. Blood from healthy individuals was collected at the moment of donation. Total RNA was extracted from blood samples using the PAXgene Blood RNA System (PreAnalytix, Hombrechtikon, Switzerland). The evaluation of concentration and quality was performed by spectrometry (NanoDrop ND1000, NanoDrop Technologies, Wilminton, Delaware USA) and RNA Experion Bioanalyzer (BioRad, California USA). Only samples with good quality and concentration were tested by ddPCR.
Quantification of Transcriptomic Response by ddPCR:

Gene expression was quantified by droplet digital PCR (ddPCR, Bio-Rad, California, USA) using predesigned TaqMan® Assay Primer/Probe Sets, (FAM labelled MGB probes, Thermo Fisher/Scientific-Life Technologies, Waltham, MA, USA): MMP8, matrix metallopeptidase 8 (neutrophil collagenase) (Reference Hs01029057_m1).

cDNA was generated from each sample on a Techne TC-512 thermal cycler (Bibby-Scientific, Staffordshire, OSA, UK) starting from 1000 ng of mRNA by using iScript™ Advanced cDNA Synthesis Kit (Biorad, California, USA, cat: 1725038). The obtained volume of cDNA (20

μl) was further diluted (½₅), and 2.5 μl (5 ng of total mRNA) were employed for quantification of target gene expression according to the manufacturer instructions.

Briefly, ddPCR was performed using the Bio-Rad QX200™ Droplet Digital™ PCR system, ddPCR™ Supermix for Probes (No dUTP), and Bio-Rad standard reagents for droplet generation and reading. End-point PCR with 40 cycles was performed by using C1000 Touch™ Thermal Cycler (BioRad, California, USA) after splitting each sample into about 20000 droplets. Next, the droplet reader used at least 10000 droplets to determine the percentage of positive droplets and calculation of copy number of cDNA per ng of initial mRNA.

Statistical Analysis:

Differences in demographic and clinical characteristics between patient groups were assessed using the $\chi2$ test for categorical variables and the Mann Whitney U test for continuous variables. Differences in gene expression levels and expression ratios were assessed using Mann Whitney U test. The accuracy of individual genes and gene expression ratios for identifying the presence/absence of sepsis was studied by calculating areas under the receiver operating characteristic curve (AUROC).

The optimal operating point (OOP) was the value for which the point on the curve had the minimum distance to the upper left corner (where sensitivity=1 and specificity=1). Categorical variables were further created using the OOPs as cut-offs. The ability of these categorical variables to diagnose the presence/absence of sepsis was further evaluated by using logistic regression analysis. Those variables yielding a p value<0.1 in the univariate regression analysis were included in the multivariate one. Logistic regression was employed also to evaluate potential associations between gene expression levels and risk of hospital mortality in sepsis patients. Napierian logarithm values of gene expression levels were employed for this analysis.

Clinical Characteristics of the Patients:

Elderly male predominated in both sepsis cases and SIRS, sepsis patients were slightly older. Profile of comorbidities was similar between sepsis cases and SIRS, but the former showed a higher prevalence of diabetes mellitus. Sepsis patients stayed longer at the hospital/ICU, presented with a higher degree of organ failure as assessed by the SOFA score. None of the patients of the SIRS control group died, but ¼ of sepsis patients did not survive to the disease. Most common sources of infection were the abdominal and respiratory ones. Sepsis patients showed a slightly higher frequency of positive cultures for Gram− than for Gram+ bacteria. Fungal infection was present in 6.9% of the sepsis patients, and viral infection was uncommon. Sepsis patients showed higher levels of C reactive protein and procalcitonin (PCT), higher counts in blood of leukocytes, neutrophils, eosinophils and basophils. Both cases and controls had lymphocyte median levels close to lymphopenia (<1000 lymphocytes/mm³).

Variation of Gene Expression and Ratios Across Groups:

As is evident in FIG. 1b, the SIRS control group presented significantly higher concentrations of MMP8 (and PCT) than healthy controls, reflecting the existence of an active inflammatory process at the systemic level in SIRS patients with no infection. Of note, is that the data shown in FIG. 1 demonstrates significant differences in MMP-8 levels between SIRS patients (model for patients with systemic inflammation) compared to patients with infections (sepsis). Although SIRS controls show up-regulation of MMP-8 over healthy subjects, and show symptoms of systemic inflammation, the MMP-8 levels determined were significantly lower when compared to patients in which an infection (sepsis) was evident.

PCT levels were also determined in parallel using protein determination via an ELISA assay. As shown in the table in FIG. 1c, the combined analysis of PCT and MMP-8 leads to higher AUROC and more significant p values when compared to the measurement of MMP-8 alone.

Additional Data for Example 1:

Patients with Sepsis Show Increased Levels of MMP-8 Over Control Groups with SIRS, as Measured Using MMP8 and PCT ELISA Patients:

56 adult patients (>18 years old) were assessed in the study. 17 uninfected SIRS patients were recruited as control group with no sepsis. 39 patients were diagnosed as septic patients (according to the definition proposed by the American College of Chest Physicians/Society of Critical Care Medicine Consensus Conference).

Statistical Analysis:

The accuracy of individual protein concentration of PCT and MMP8 and combination of both for identifying the presence/absence of sepsis was studied by calculating areas under the receiver operating characteristic curve (AUROC). Each point on the ROC curve represents a sensitivity/specificity pair corresponding to a particular decision threshold/cutoff (table 2). The youden's index was calculated for each cutoff and the highest index depicts the cutoff with the best possible sensitivity/specificity pair. For example, if a clinician wants to use the MMP8 to rule out sepsis, a sensitivity of 100% is preferred, that would in this example correspond to a cutoff of 3.28 ng/ml. To rule-in sepsis, a specificity of 100% (cutoff 43.68 ng/ml) is preferred.

Absolute MMP8 concentrations may vary depending on differences in absolute quantities determined in different assay formats (see example 3), therefore fold changes were calculated to estimate the difference between sepsis and controls, independent of the test system.

Fold changes were estimated using an ANOVA model of log 2-transformed biomarker values. The difference of means and a corresponding confidence interval of the log 2-transformed values in the two groups was estimated using least square means. Then the inverse transformation $2^{difference\ of\ means}$ gives an estimate of the fold change and the corresponding confidence limits because $$2^{log_2(x)-log_2(y)} = \frac{2^{log_2(x)}}{2^{log_2(y)}} = \frac{x}{y}.$$

FIG. 2 shows a ROC curve for measurements of PCT and/or MMP8 using ELISA. As demonstrated in FIG. 2, MMP8 alone, PCT alone and MMP8 and PCT in combination show good specificity and sensitivity and demonstrate significant differences in MMP-8 and/or PCT levels between SIRS patients (model for patients with systemic inflammation) compared to patients with infections (sepsis).

TABLE 1

Fold changes with 95% confidence interval (95% CI), comparing PCT or MMP8 levels in sepsis patients compared to SIRS patients.

| Model | FoldChange | 95% CI | p-value |
|---|---|---|---|
| PCT | 15.55 | [4.88-49.51] | 0.00002 |
| MMP8-ELISA | 3.63 | [1.84-7.16] | 0.00036 |

TABLE 2

Sensitivity, specificity and youden index for all possible cutoffs calculated by ROC analyses. Optimal combination of sensitivity and specificity is represented by the highest youden index. To rule out sepsis, e.g. a sensitivity of 100% (cutoff 3.28 ng/mL) is preferred, to rule-in sepsis, e.g. a specifity of 100% (cutoff 43.68 ng/mL) is preferred. The highest combined values for sensitivity and specificity (highest youden index) is marked in bold type.

| Cutoff MMP 8 ELISA [ng/ml] | Sensitivity | Specificity | Youden |
|---|---|---|---|
| 3.28 | 1.000 | 0.059 | 0.059 |
| 3.55 | 0.974 | 0.059 | 0.033 |
| 3.82 | 0.949 | 0.059 | 0.008 |
| 4.26 | 0.949 | 0.118 | 0.066 |
| 4.29 | 0.949 | 0.176 | 0.125 |
| 4.43 | 0.949 | 0.235 | 0.184 |
| 6.15 | 0.923 | 0.235 | 0.158 |
| 6.16 | 0.923 | 0.294 | 0.217 |
| 6.61 | 0.897 | 0.294 | 0.192 |
| 7.08 | 0.897 | 0.353 | 0.250 |
| 7.40 | 0.872 | 0.353 | 0.225 |
| 8.34 | 0.872 | 0.412 | 0.284 |
| 8.90 | 0.872 | 0.471 | 0.342 |
| 9.73 | 0.846 | 0.471 | 0.317 |
| 10.07 | 0.821 | 0.471 | 0.291 |
| 10.86 | 0.821 | 0.529 | 0.350 |
| 11.24 | 0.795 | 0.529 | 0.324 |
| 11.49 | 0.769 | 0.529 | 0.299 |
| 13.46 | 0.744 | 0.529 | 0.273 |
| 14.26 | 0.744 | 0.588 | 0.332 |
| 19.36 | 0.744 | 0.647 | 0.391 |
| 19.55 | 0.744 | 0.706 | 0.449 |
| 21.19 | 0.718 | 0.706 | 0.424 |
| 22.46 | 0.718 | 0.765 | 0.483 |
| 22.58 | 0.692 | 0.765 | 0.457 |
| 22.65 | 0.692 | 0.824 | 0.516 |
| 24.67 | 0.692 | 0.882 | 0.575 |
| 25.36 | 0.667 | 0.882 | 0.549 |
| 25.75 | 0.641 | 0.882 | 0.523 |
| 27.33 | 0.615 | 0.882 | 0.498 |
| 27.99 | 0.590 | 0.882 | 0.472 |
| 29.27 | 0.564 | 0.882 | 0.446 |
| 29.37 | 0.538 | 0.882 | 0.421 |
| 29.78 | 0.513 | 0.882 | 0.395 |
| 31.24 | 0.487 | 0.882 | 0.370 |
| 36.68 | 0.487 | 0.941 | 0.428 |
| 43.60 | 0.462 | 0.941 | 0.403 |
| 43.68 | 0.462 | 1.000 | 0.462 |
| 43.72 | 0.436 | 1.000 | 0.436 |
| 54.24 | 0.410 | 1.000 | 0.410 |
| 62.60 | 0.385 | 1.000 | 0.385 |
| 72.96 | 0.359 | 1.000 | 0.359 |
| 75.80 | 0.333 | 1.000 | 0.333 |
| 84.40 | 0.308 | 1.000 | 0.308 |
| 91.60 | 0.282 | 1.000 | 0.282 |
| 92.76 | 0.256 | 1.000 | 0.256 |
| 100.52 | 0.231 | 1.000 | 0.231 |
| 125.04 | 0.205 | 1.000 | 0.205 |
| 136.20 | 0.179 | 1.000 | 0.179 |
| 148.84 | 0.154 | 1.000 | 0.154 |
| 172.28 | 0.128 | 1.000 | 0.128 |
| 209.20 | 0.103 | 1.000 | 0.103 |
| 243.16 | 0.077 | 1.000 | 0.077 |
| 320.00 | 0.051 | 1.000 | 0.051 |
| 320.00 | 0.051 | 1.000 | 0.051 |

Example 2

Patients with Sepsis Show Increased Levels of MMP-8 Over Control Groups of Patients Having Undergone Surgery Patients:

In a similar study to Example 1 above, 101 adult patients (>18 years old) admitted to the Surgery Service or to the Surgical ICU of the participant hospitals with a diagnosis of sepsis (according to the definition proposed by the American College of Chest Physicians/Society of Critical Care Medicine Consensus Conference) were recruited. 53 uninfected surgical patients were recruited as control group with no sepsis. In addition, 16 blood donors of similar age of the patients were recruited as healthy controls.

Sepsis patients were in need of urgent surgery in ⅔ of the cases, while this was a rare event in controls. Kind of surgery was similar in both groups. Sepsis patients stayed longer at the hospital/ICU, presented with a higher degree of organ failure as assessed by the SOFA score. None of the patients of the surgical control group died, but ¼ of sepsis patients did not survive to the disease.

Methods for ddPCR, ELISA and statistical analyses were performed essentially as in Example 1.

Variation of Gene Expression and Ratios Across Groups:

As is evident from Table 3 below, surgical controls presented significantly higher concentrations of PCT and MMP8 than healthy controls, reflecting the existence of an active inflammatory process at the systemic level in post-operated patients with no infection. Of note, is that the data shown below in table 3 demonstrates significant differences in both MMP-8 and PCT levels between surgical controls ((1); model for patients with systemic inflammation) compared to patients with infections ((2); sepsis). Although surgical controls show up-regulation of MMP-8 over healthy subjects, and show symptoms of systemic inflammation, the MMP-8 levels determined were significantly lower when compared to patients in which an infection (sepsis) was evident.

TABLE 3

Comparison of gene expression levels, procalcitonin levels and ratios between groups.

| | Healthy Controls (0) | Surgical Controls (1) | Sepsis SOFA < 8 (2) | Sepsis SOFA ≥ 8 (3) | p (0 vs 1) | p (0 vs 2) | p (0 vs 3) | P (1 vs 2) | p (1 vs 3) | p (2 vs 3) |
|---|---|---|---|---|---|---|---|---|---|---|
| MMP8 | 23 [68] | 125 [302] | 856 [4169] | 5116 [12636] | <0.001 | <0.001 | < 0.001 | <0.001 | <0.001 | <0.001 |
| PCT | 0.03 [0.02] | 0.50 [0.97] | 1.63 [5.25] | 12.09 [50.46] | <0.001 | <0.001 | < 0.001 | <0.001 | <0.001 | <0.001 |
| (MMP8 + PCT) * | N. A | 0.3 [0.4] | 0.8 [0.3] | 1.0 [0.1] | N. A | N. A | N. A | <0.001 | <0.001 | <0.001 |

Table 3: Comparison of gene expression levels, procalcitonin levels and ratios between groups.
Results for gene expression levels are provided as cDNA copies/ng total mRNA.
Results for PCT are provided as ng/mL.
The values shown above for each data row relate to the measured mean values for each marker in each patient group (either cDNA copies/ng total mRNA or ng/mL).
The values shown in square brackets relate to the median interquartile range (IQR).
* Results from a probabilistic function built using logistic regression combining MMP8 and PCT levels to distinguish sepsis from no sepsis patients.
Log values of PCT and MMP8 were used for building this function, since neither MMP8 not PCT values followed a normal distribution.
N.A: not applicable.

Further analysis of MMP-8 protein levels via immunoassays (e. g. Luminex) confirms the results above.

Example 3

Patients with Sepsis Show Increased Levels of MMP-8 Over Control Groups with Dyspnea
Patients:
68 adult patients (>18 years old) were assessed in the study. 21 patients with dyspnea were recruited as control group. 22 patients with sepsis and 25 patients with severe sepsis were recruited (according to the definition proposed by the American College of Chest Physicians/Society of Critical Care Medicine Consensus Conference).
Statistical Analysis:
As described for example 1.
Results:
MMP8 levels were also determined in parallel using protein determination via an ELISA and a Luminex MAG-PIX assay. As shown in FIGS. 3 and 4, and Tables 4, 5 and 6 below, the combined analysis of PCT and MMP-8 leads to higher AUROC and more significant p values when compared to the measurement of MMP-8 alone.

TABLE 4

$\chi^2$ test statistics for PCT, two different MMP8 assays, and the PCT + MMP8 combinations. Addition of MMP8 to PCT shows a significant add-on to diagnose sepsis, independent of the MMP8 assay type.

| | N | Events | LR Chi2 | DF | p value | C Index | added LR Chi2 | added DF | added p value |
|---|---|---|---|---|---|---|---|---|---|
| PCT | 68 | 47 | 23.16 | 1 | 0.00000 | 0.837 | | | |
| MMP8-Luminex | 68 | 47 | 19.45 | 1 | 0.00001 | 0.819 | | | |
| MMP8-ELISA | 68 | 47 | 36.30 | 1 | 0.00000 | 0.903 | | | |
| PCT + MMP8-Luminex | 68 | 47 | 33.04 | 2 | 0.00000 | 0.905 | 9.88 | 1 | 0.00167 |
| PCT + MMP8-ELISA | 68 | 47 | 44.82 | 2 | 0.00000 | 0.933 | 21.66 | 1 | 0.00000 |

DF = degree of freedom

With respect to mean fold changes, MMP-8 and PCT levels were compared in patient groups with sepsis, dyspnea and severe sepsis, in order to determine whether mean fold change values between the population groups could be determined.

TABLE 5

Fold changes with 95% confidence interval (95% CI).

| | Contrast | Fold change | 95% CI | p value |
|---|---|---|---|---|
| PCT | Sepsis - Dyspnea | 3.53 | [1.09-11.39] | 0.03238 |
| PCT | Severe Sepsis - Dyspnea | 16.99 | [5.45-53.00] | 0.00000 |
| MMP8-Luminex | Sepsis - Dyspnea | 4.27 | [1.75-10.43] | 0.00068 |
| MMP8-Luminex | Severe Sepsis - Dyspnea | 4.48 | [1.88-10.65] | 0.00029 |
| MMP8-ELISA | Sepsis - Dyspnea | 2.75 | [1.59-4.73] | 0.00010 |
| MMP8-ELISA | Severe Sepsis - Dyspnea | 5.77 | [3.40-9.78] | 0.00000 |

With respect to mean fold changes, MMP-8 and PCT levels were compared in patients groups with sepsis, dyspnea and severe sepsis, in order to determine whether mean fold change values between the population groups could be determined. The analysis showed 2.75 to 4.27-fold increased MMP-8 in sepsis vs. dyspnea 3.53-fold increased PCT in sepsis vs. dyspnea 4.48 to 5.77-fold increased MMP-8 in severe sepsis vs. dyspnea 16.99-fold increased PCT in severe sepsis vs. dyspnea As is evident from the above, patients with dyspnea (shortness of breath; a control group for patients with a systemic inflammatory condition but without an infection) showed reduced levels in both MMP-8 and PCT compared to patients with sepsis (patients with an infection).

TABLE 6

Sensitivity, specificity and youden index for all possible cutoffs calculated by ROC analyses. Optimal combination of sensitivity and specificity is represented by the highest youden index (bold type). For example, to rule out sepsis a sensitivity of 100% is preferred, to rule-in sepsis a specifity of 100% is preferred.

| MMP8-Luminex [pg/mL] | | | | MMP8-ELISA [pg/mL] | | | |
|---|---|---|---|---|---|---|---|
| Cutoff | Sensitivity | Specificity | Youden | Cutoff | Sensitivity | Specificity | Youden |
| 32.98 | 0.957 | 0.095 | 0.053 | 8892.00 | 1.000 | 0.048 | 0.048 |
| 34.39 | 0.936 | 0.095 | 0.031 | 9292.00 | 1.000 | 0.095 | 0.095 |
| 34.39 | 0.936 | 0.095 | 0.031 | 9360.00 | 1.000 | 0.143 | 0.143 |
| 42.04 | 0.915 | 0.143 | 0.058 | 10364.00 | 1.000 | 0.190 | 0.190 |
| 42.89 | 0.915 | 0.190 | 0.105 | 11568.00 | 1.000 | 0.238 | 0.238 |
| 45.73 | 0.915 | 0.238 | 0.153 | 13160.00 | 1.000 | 0.286 | 0.286 |
| 50.02 | 0.915 | 0.286 | 0.201 | 15716.00 | 1.000 | 0.333 | 0.333 |
| 62.92 | 0.915 | 0.333 | 0.248 | 15812.00 | 0.979 | 0.333 | 0.312 |
| 63.08 | 0.915 | 0.381 | 0.296 | 16500.00 | 0.957 | 0.333 | 0.291 |
| 68.72 | 0.915 | 0.429 | 0.343 | 16832.00 | 0.957 | 0.381 | 0.338 |
| 69.41 | 0.894 | 0.429 | 0.322 | 17572.00 | 0.957 | 0.429 | 0.386 |
| 69.43 | 0.872 | 0.429 | 0.301 | 17836.00 | 0.957 | 0.476 | 0.434 |
| 70.15 | 0.851 | 0.429 | 0.280 | 20804.00 | 0.957 | 0.524 | 0.481 |
| 74.48 | 0.830 | 0.429 | 0.258 | 22448.00 | 0.936 | 0.524 | 0.460 |
| 79.13 | 0.830 | 0.476 | 0.306 | 22592.00 | 0.936 | 0.571 | 0.508 |
| 83.21 | 0.809 | 0.476 | 0.285 | 23220.00 | 0.915 | 0.571 | 0.486 |
| 88.10 | 0.787 | 0.476 | 0.263 | 23548.00 | 0.915 | 0.619 | 0.534 |
| 91.91 | 0.787 | 0.524 | 0.311 | 24660.00 | 0.894 | 0.619 | 0.513 |
| 96.29 | 0.787 | 0.571 | 0.359 | 25488.00 | 0.894 | 0.667 | 0.560 |
| 96.61 | 0.787 | 0.619 | 0.406 | 25544.00 | 0.872 | 0.667 | 0.539 |
| 97.89 | 0.787 | 0.667 | 0.454 | 27300.00 | 0.872 | 0.714 | 0.587 |
| 98.86 | 0.787 | 0.714 | 0.502 | 28148.00 | 0.872 | 0.762 | 0.634 |
| 102.87 | 0.787 | 0.762 | 0.549 | 28612.00 | 0.851 | 0.762 | 0.613 |
| 106.54 | 0.766 | 0.762 | 0.528 | 28980.00 | 0.830 | 0.762 | 0.592 |
| 118.94 | 0.766 | 0.810 | 0.575 | 29792.00 | 0.830 | 0.810 | 0.639 |
| 138.72 | 0.766 | 0.857 | 0.623 | 31148.00 | 0.809 | 0.810 | 0.618 |
| 162.31 | 0.745 | 0.857 | 0.602 | 31724.00 | 0.787 | 0.810 | 0.597 |
| 167.16 | 0.723 | 0.857 | 0.581 | 33424.00 | 0.766 | 0.810 | 0.575 |
| 173.12 | 0.702 | 0.857 | 0.559 | 38052.00 | 0.766 | 0.857 | 0.623 |
| 192.24 | 0.681 | 0.857 | 0.538 | 38920.00 | 0.766 | 0.905 | 0.671 |
| 207.95 | 0.681 | 0.905 | 0.586 | 42280.00 | 0.745 | 0.905 | 0.649 |
| 211.60 | 0.681 | 0.952 | 0.633 | 48080.00 | 0.723 | 0.905 | 0.628 |
| 217.71 | 0.660 | 0.952 | 0.612 | 48960.00 | 0.723 | 0.952 | 0.676 |
| 220.35 | 0.638 | 0.952 | 0.591 | 53480.00 | 0.702 | 0.952 | 0.655 |
| 254.52 | 0.617 | 0.952 | 0.569 | 55480.00 | 0.681 | 0.952 | 0.633 |
| 258.28 | 0.596 | 0.952 | 0.548 | 56400.00 | 0.660 | 0.952 | 0.612 |
| 280.89 | 0.574 | 0.952 | 0.527 | 59640.00 | 0.638 | 0.952 | 0.591 |
| 302.83 | 0.553 | 0.952 | 0.506 | 63120.00 | 0.617 | 0.952 | 0.569 |
| 318.25 | 0.532 | 0.952 | 0.484 | 68560.00 | 0.596 | 0.952 | 0.548 |
| 353.50 | 0.511 | 0.952 | 0.463 | 72040.00 | 0.574 | 0.952 | 0.527 |

TABLE 6-continued

Sensitivity, specificity and youden index for all possible cutoffs calculated by ROC analyses. Optimal combination of sensitivity and specificity is represented by the highest youden index (bold type). For example, to rule out sepsis a sensitivity of 100% is preferred, to rule-in sepsis a specifity of 100% is preferred.

| MMP8-Luminex [pg/mL] | | | | MMP8-ELISA [pg/mL] | | | |
|---|---|---|---|---|---|---|---|
| Cutoff | Sensitivity | Specificity | Youden | Cutoff | Sensitivity | Specificity | Youden |
| 399.94 | 0.489 | 0.952 | 0.442 | 72480.00 | 0.553 | 0.952 | 0.506 |
| 481.98 | 0.468 | 0.952 | 0.420 | 72640.00 | 0.553 | 1.000 | 0.553 |
| 530.84 | 0.447 | 0.952 | 0.399 | 73680.00 | 0.532 | 1.000 | 0.532 |
| 538.81 | 0.426 | 0.952 | 0.378 | 77640.00 | 0.511 | 1.000 | 0.511 |
| 568.13 | 0.404 | 0.952 | 0.357 | 78480.00 | 0.489 | 1.000 | 0.489 |
| 580.18 | 0.383 | 0.952 | 0.335 | 83160.00 | 0.468 | 1.000 | 0.468 |
| 685.58 | 0.383 | 1.000 | 0.383 | 85280.00 | 0.447 | 1.000 | 0.447 |
| 728.74 | 0.362 | 1.000 | 0.362 | 89800.00 | 0.426 | 1.000 | 0.426 |
| 769.54 | 0.340 | 1.000 | 0.340 | 91320.00 | 0.404 | 1.000 | 0.404 |
| 835.26 | 0.319 | 1.000 | 0.319 | 92200.00 | 0.383 | 1.000 | 0.383 |
| 837.23 | 0.298 | 1.000 | 0.298 | 110840.00 | 0.362 | 1.000 | 0.362 |
| 855.38 | 0.277 | 1.000 | 0.277 | 112520.00 | 0.340 | 1.000 | 0.340 |
| 880.72 | 0.255 | 1.000 | 0.255 | 121280.00 | 0.319 | 1.000 | 0.319 |
| 957.64 | 0.234 | 1.000 | 0.234 | 127760.00 | 0.298 | 1.000 | 0.298 |
| 969.63 | 0.213 | 1.000 | 0.213 | 133680.00 | 0.277 | 1.000 | 0.277 |
| 1013.76 | 0.191 | 1.000 | 0.191 | 173480.00 | 0.255 | 1.000 | 0.255 |
| 1120.33 | 0.170 | 1.000 | 0.170 | 176800.00 | 0.234 | 1.000 | 0.234 |
| 1173.56 | 0.149 | 1.000 | 0.149 | 180120.00 | 0.213 | 1.000 | 0.213 |
| 1206.70 | 0.128 | 1.000 | 0.128 | 184320.00 | 0.191 | 1.000 | 0.191 |
| 1346.59 | 0.106 | 1.000 | 0.106 | 185560.00 | 0.170 | 1.000 | 0.170 |
| 1430.56 | 0.085 | 1.000 | 0.085 | 214120.00 | 0.149 | 1.000 | 0.149 |
| 1855.90 | 0.064 | 1.000 | 0.064 | 221240.00 | 0.128 | 1.000 | 0.128 |
| 4161.58 | 0.043 | 1.000 | 0.043 | 246960.00 | 0.106 | 1.000 | 0.106 |
| 6459.76 | 0.021 | 1.000 | 0.021 | 258880.00 | 0.085 | 1.000 | 0.085 |

The invention claimed is:

1. A method for diagnosis and treatment of bacterial sepsis, severe sepsis and/or septic shock in a subject, wherein said method comprises:
   providing a sample from said subject wherein the subject has symptoms of a systemic inflammatory response syndrome (SIRS) or dyspnea;
   measuring the metalloprotease-8 (MMP-8) in the sample from said subject,
   wherein when the level of MMP-8 in the sample of said subject is above a reference level, threshold value and/or a population average corresponding to MMP-8 level in subjects with a systemic inflammatory response syndrome (SIRS) or dyspnea without an infection, the said level of MMP-8 being indicative of the presence of a bacterial sepsis, severe sepsis, and/or septic shock in said subject, the method comprises administering to said subject an effective amount of an antibiotic.

2. The method according to claim 1, further comprising measuring the level of procalcitonin (PCT) in said sample of the subject and determining if the level of PCT in said sample of the subject is above a reference level corresponding to PCT levels in subjects with a systemic inflammatory response syndrome (SIRS) or dyspnea without an infection.

3. The method according to claim 1, wherein the systemic inflammatory response syndrome (SIRS) without an infection is SIRS without infection by a pathogenic agent or microorganism.

4. The method according to claim 1, wherein the sample is provided within 72 hours after symptoms of an infectious disease and/or systemic inflammatory response syndrome (SIRS) occur in the subject.

5. The method according to claim 1, wherein the subject is a post-surgery subject.

6. The method according to claim 1, wherein the subject suffers from shortness of breath.

7. The method according to claim 1, wherein the sample is a blood sample or a sample derived from blood, plasma or serum.

8. The method according to claim 1, wherein the level of MMP-8 is measured by measuring MMP-8 gene expression by detecting MMP-8 encoding RNA or cDNA corresponding thereto.

9. The method according to claim 8, wherein measuring MMP-8 gene expression comprises a quantitative nucleic acid amplification reaction.

10. The method according to claim 1, additionally comprising determining one or more additional markers selected from the group consisting of adrenomedullin (ADM), pro-adrenomedullin, histone H2A, histone H2B, histone H3, histone H4, procalcitonin, calcitonin, endothelin-1 (ET-1), arginine vasopressin (AVP), atrial natriuretic peptide (ANP), neutrophil gelatinase-associated lipocalin (NGAL), troponin, brain natriuretic peptide (BNP), c-reactive protein (CRP), pancreatic stone protein (PSP), triggering receptor expressed on myeloid cells 1 (TREM1), interleukin-6 (IL-6), interleukin-1, interleukin-24 (IL-24) other ILs, presepsin (sCD14-ST), lipopolysaccharide binding protein (LBP), alpha-1-antitrypsin, matrix metalloproteinase 2 (MMP2), matrix metalloproteinase 9 (MMP9), matrix metalloproteinase 7 (MMP9), soluble fms-like tyrosine kinase-1 (sFlt-1), placental growth factor (PlGF), chromogranin A, S100A protein, S100B protein and tumor necrosis factor α (TNFα), lipocalin-2 (LCN2), olfactomedin 4 (OLFM4) and proteinase 3 (PRTN3) or a fragment thereof.

11. The method according to claim 9, wherein the quantitative nucleic acid amplification reaction is real-time PCR (RT-PCR) or digital droplet PCR (ddPCR) employing detection of cDNA corresponding to MMP-8 encoding mRNA.

12. The method according to claim 1, wherein the level of MMP-8 is at least 2-fold above the reference level, threshold value, and/or population average.

* * * * *